United States Patent [19]

Cate et al.

[11] Patent Number: 5,427,780
[45] Date of Patent: Jun. 27, 1995

[54] COMPOSITION COMPRISING MULLERIAN INHIBITING SUBSTANCE-LIKE POLYPEPTIDES

[75] Inventors: Richard L. Cate, Brookline; Patricia K. Donahoe, Weston, both of Mass.

[73] Assignees: Biogen, Inc., Netherlands Antilles; The General Hospital Corporation, Boston, Mass.

[21] Appl. No.: 957,061

[22] Filed: Oct. 5, 1992

Related U.S. Application Data

[63] Continuation of Ser. No. 693,764, Apr. 25, 1991, abandoned, which is a continuation of Ser. No. 923,879, Oct. 28, 1986, abandoned, which is a continuation-in-part of Ser. No. 792,880, Oct. 30, 1985, Pat. No. 5,047,336.

[51] Int. Cl.$^6$ .................... C07K 15/00; A61K 37/02
[52] U.S. Cl. .................... 424/85.1; 530/399; 530/351; 514/12
[58] Field of Search ............ 530/351, 350, 399, 397; 514/8, 12; 424/85.1

[56] References Cited

U.S. PATENT DOCUMENTS

| | | | |
|---|---|---|---|
| 4,289,690 | 9/1981 | Pestka et al. | 260/112 R |
| 4,404,188 | 9/1983 | Donahoe et al. | 424/105 |
| 4,442,205 | 4/1984 | Hamer et al. | 435/172.2 |
| 4,487,833 | 12/1984 | Donahoe et al. | 435/172.2 |
| 4,510,131 | 4/1985 | Donahoe et al. | 424/105 |
| 4,740,587 | 4/1988 | Ling et al. | 530/351 |
| 4,753,794 | 6/1988 | Donahoe | 424/85 |
| 4,792,601 | 12/1988 | Donahoe et al. | 530/387 |
| 5,010,055 | 4/1991 | Donahoe | 514/8 |
| 5,011,687 | 4/1991 | Donahoe et al. | 424/559 |
| 5,047,336 | 9/1991 | Cate et al. | 435/69.4 |
| 5,198,420 | 3/1993 | Donahoe et al. | 424/85.8 |

OTHER PUBLICATIONS

Hird et al. *Genes and Cancer* pp. 183–189 (1990).
Bowie et al *Science* 247:1306–1310 (1990).
Chem. Abstr. vol. 99 (1983) 116305.
Chem. Abstr. vol. 90 (1979) 199833.
Chem. Abstr. vol. 107 (1987) 230569.
Chem. Abstr. vol. 107 (1987) 110364.
M. G. Blanchard et al., "Source of The Anti–Mullerian Hormone Synthesized By The Fetal Testis: Mullerian–Inhibiting Activity Of Fetal Bovine Sertoli Cells In Tissue Culture", *Pediat. Res.*, 8, 968–971 (1974).
G. Budzik et al., "Enhanced Purification Of Mullerian Inhibiting Substance By Lectin Affinity Chromatography", *Cell*, 21, 909–915 (1980) [Budzik et al. I].
G. Budzik et al., "A Possible Purification Of Mullerian Inhibiting Substance And A Model For Its Mechanism Of Action", *Developmental Mechanisms: Normal and Abnormal*, 171, 207–223 (1985) [Budzik et al. II].
R. L. Cate et al., "Isolation Of The Bovine And Human Genes For Mullerian Inhibiting Substance And Expression Of The Human Gene In Animal Cells", *Cell*, 45, pp. 685–698 (1986).
P. Donahoe et al., "The Production Of Mullerian Inhibiting Substance By The Fetal, Neonatal And Adult Rat", *Biology of Reproduction*, 15, 329–334 (1976) [Donahoe et al. I].
P. Donahoe et al., "Mullerian Inhibiting Substance Activity In Bovine Fetal, Newborn And Prepubertal Testes", *Biology of Reproduction*, 16, 238–243 (1977) [Donahoe et al. II].
P. Donahoe et al., "Mullerian Inhibiting Substance In Human Testes After Birth", *Journal of Pediatric Surgery*, 12, 323–330 (1977) [Donahoe et al. III].

(List continued on next page.)

*Primary Examiner*—Garnette D. Draper
*Assistant Examiner*—Shelly Guest Cermak
*Attorney, Agent, or Firm*—Sterne, Kessler, Goldstein & Fox

[57] ABSTRACT

Mullerian Inhibiting Substance (MIS)-like polypeptide are described. The MIS-like polypeptides are useful in the treatment of ovarian cancer and other susceptible cancers.

1 Claim, 26 Drawing Sheets

OTHER PUBLICATIONS

P. Donahoe et al., "Mullerian Duct Regression In The Embryo Correlated With Cytotoxic Activity Against Human Ovarian Cancer", *Science*, 205, 913–915 (1979) [Donahoe et al. IV].

P. Donahoe et al., "Mullerian Inhibiting Substance Inhibits Growth Of A Human Ovarian Cancer In Nude Mice", *Ann. Surg.*, 194, 472–480 (1981) [Donahoe et al. V].

P. Donahoe et al., "The Biochemistry And Biology Of Mullerian Inhibiting Substance", *Pediatric Andrology*, 37–46, 1981 [Donahoe et al. VI].

P. Donahoe et al., "Mullerian-Inhibiting Substance: An Update", *Recent Progress In Hormone Research*, 38, 279–330 (1982). [Donahoe et al. VII].

P. Donahoe et al., "Mechanism Of Action Of Mullerian Inhibiting Substance", *Ann. Rev. Physiol.*, 46, 53–65 (1984). [Donahoe et al. VIII].

P. Donahoe et al., "Molecular Dissection Of Mullerian Duct Regression", *The Role of Extracellular Matrix in Development*, 573–595 (1984) [Donahoe et al. IX].

M. Fallat et al., "The Role of Nucleotide Pyrophosphatase In Mullerian Duct Regression", *Developmental Biology*, 100, 358–364 (1983) [Fallat et al. I].

M. Fallat et al., "Androgen Stimulation Of Nucelotide Pyrophosphatase During Mullerian Duct Regression", *Endocrinology*, 114, 1592–1598 (1984) [Fallat et al. II].

A. Fuller, Jr. et al., "Mullerian Inhibiting Substance Inhibits Colony Growth Of A Human Ovarian Carcinoma Cell Line", *J. Clin. Endocr. Met.*, 54, 1051–1055 (1982) [Fuller et al. I].

A. Fuller, Jr. et al., "Mullerian Inhibiting Substance Inhibition Of A Human Endometrial Carcinoma Cell Line Xenografted In Nude Mice", *Gynecologic Oncology*, 17, 124–132 (1984) [Fuller et al. II].

A. Fuller, Jr. et al., "Mullerian Inhibiting Substance Reduction Of Colony Growth Of Human Gynecologic Cancers In A Stem Cell Assay", *Gynecologic Oncology*, 22, 135–148 (1985) [Fuller et al. III].

M. Hayashi et al., "Immunocytochemical Localization Of Mullerian Inhibiting Substance In The Rough Endoplasmic Reticulum And Golgi Apparatus In Sertoli Cells Of The Neonatal Calf Testis Using A Monoclonal Antibody", *Journal of Histochemistry and Cytochemistry*, 32, 649–654 (1984).

J. Hutson et al., "The Ontogeny Of Mullerian Inhibiting Substance In The Gonads Of The Chicken", *J. Pediatric Surgery*, 16, 822–827 (1981) [Hutson et al. I].

J. Hutson et al., "Phosphorylation Events During Mullerian Duct Regression", *Science*, 223, 586–589, (1984) [Hutson et al. II].

J. Hutson et al., "Steroid Modulation Of Mullerian Duct Regression In The Chick Embryo", *General and Comparative Endocrinology*, 57, 88–102 (1985) [Hutson et al. III].

H. Ikawa et al., "Steroid Enhancement Of Mullerian Duct Regression", *J. Pediatric Surgery*, 17, 453–458 (1982) [Ikawa et al. I].

H. Ikawa et al., "Cyclic Adenosine 3',5'-Monophosphate Modulation Of Mullerian Duct Regression", *Endocrinology*, 114, 1686–1691 (1984) [Ikawa et al. II].

M. Jaye et al., "Isolation Of A Human Anti-Haemophilic Factor IX cDNA Clone Using A Unique 52-Base Synthetic Oligonucleotide Probe Deduced From The Amino Acid Sequence Of Bovine Factor IX", *Nucleic Acids Research*, 11, pp. 2325–2335 (1983).

N. Josso, "Permeability Of Membranes To The Mullerian-Inhibiting Substance Synthesized By The Human Fetal Testis in Vitro: A Clue To Its Biochemical Nature", *J. Clin. Endocr.*, 34, 265–270 (1972) [Josso I].

N. Josso, "In Vitro Synthesis Of Mullerian-Inhibiting Hormone By Seminiferous Tubules Isolated From The Calf Fetal Testis", *Endocrinology*, 93, 829–834 (1973) [Josso II].

N. Josso et al., "Mullerian-Inhibiting Activity Of Calf Fetal Testes: Relationship To Testosterone And Protein Synthesis", *Biology of Reproduction*, 13, 153–167 (1975).

D. MacLaughlin et al., "Specific Estradiol Binding In Embryonic Mullerian Ducts: A Potential Modulator Of Regression In The Male And Female Chick", *Endocrinology*, 113, 141–145 (1983).

M. Mudgett-Hunter et al., "Monoclonal Antibody To Mullerian Inhibiting Substance", *Journal of Immunology*, 128, 1327–1333 (1982).

E. C. Necklaws et al., "Detection Of Mullerian Inhibiting Substance In Biological Samples By A Solid Phase Sandwich Radioimmunoassay", *Endocrinology*, 118, pp. 791–796 (1986).

J.-Y. Picard et al., "Anti-Mullerian Hormone: Estimation Of Molecular Weight By Gel Filtration", *Biomedicine*, 25, 147–150 (1976) [Picard et al. I].

(List continued on next page.)

OTHER PUBLICATIONS

J-Y Picard et al., "Biosynthesis Of Labelled Anti-Mullerian Hormone By Fetal Testes: Evidence For The Glycoprotein Nature Of The Hormone And For Its Disulfide-Bonded Structure", *Molecular and Cellular Endocrinology*, 12, 17–30, (1978) [Picard et al. II].

J-Y Picard et al., "Purification Of Testicular Anti-Mullerian Hormone Allowing Direct Visualization Of The Pure Glycoprotein And Determination Of Yield And Purification Factor", *Molecular and Cellular Endocrinology*, 34, pp. 23–29 (1984) [Picard et al. III].

Z. Rosenwaks et al., "In Vitro Inhibition Of Endometrial Cancer Growth By A Neonatal Rat Testicular Secretory Product", *J. Clin. Endocr. Met.*, 52, 817–819 (1981).

*SCRIP*, No. 976, p. 22, Feb. 25, 1985.

H. Shima et al., "Production Of Monoclonal Antibodies For Affinity Purification Of Bovine Mullerian Inhibiting Substance Activity", *Hybridoma*, 3, 201–214 (1984).

B. Vigier et al., "A Monoclonal Antibody Against Bovine Anti-Mullerian Hormone", *Endocrinology*, 110, 131–137 (1982) [Vigier et al. I].

B. Vigier et al., "Production Of Anti-Mullerian Hormone: Another Homology Between Sertoli And Granulosa Cells", *Endocrinology*, 114, 1315–1320 (1984) [Vigier et al. II].

Peak # T105-106:

LeuAspLeuValProPheProGlnPro

Peak # T81:

LeuAlaLeuAspProGlyAlaLeuAlaGlyPheProGlnGlyGlnVal

FIG. 1

```
Val Pro Phe Pro Gln Pro
5' GTN CCN TTY CCN CAR CC 3'
3' CAN GGN AAR GGN GTY GG 5'
```

| subpool sequence | | | | | | subpool # | degeneracy |
|---|---|---|---|---|---|---|---|
| 3' | CAN | GGA | AAR | GGN | GTY GG 5' | 1 | 64 |
| 3' | CAN | GGG | AAR | GGN | GTY GG 5' | 2 | 64 |
| 3' | CAN | GGT | AAR | GGN | GTY GG 5' | 3 | 64 |
| 3' | CAN | GGC | AAR | GGN | GTY GG 5' | 4 | 64 |

```
Gly Phe Pro Gln Gly Gln Val
5' GGN TTY CCN CAR GGN CAR GT 3'
3' CCN AAR GGN GTY CCN GTY CA 5'
```

| subpool sequence | | | | | | subpool # | degeneracy |
|---|---|---|---|---|---|---|---|
| 3' | CCN | AAR | GGA | GTY | CCN GTY CA 5' | 9 | 128 |
| 3' | CCN | AAR | GGG | GTY | CCN GTY CA 5' | 10 | 128 |
| 3' | CCN | AAR | GGT | GTY | CCN GTY CA 5' | 11 | 128 |
| 3' | CCN | AAR | GGC | GTY | CCN GTY CA 5' | 12 | 128 |

FIG. 2A

| subpool sequence | subpool # | degeneracy |
|---|---|---|
| 3' CAN GGG AAR GGN GTY GG 5' | | |
| 3' CAN GGG AAR GGA GTY GG 5' | 13 | 16 |
| 3' CAN GGG AAR GGG GTY GG 5' | 14 | 16 |
| 3' CAN GGG AAR GGT GTY GG 5' | 15 | 16 |
| 3' CAN GGG AAR GGC GTY GG 5' | 16 | 16 |

| subpool sequence | subpool # | degeneracy |
|---|---|---|
| 3' CCN AAR GGC GTY CCN GTY CA 5' | | |
| 3' CCN AAR GGC GTY CCA GTY CA 5' | 17 | 32 |
| 3' CCN AAR GGC GTY CCG GTY CA 5' | 18 | 32 |
| 3' CCN AAR GGC GTY CCT GTY CA 5' | 19 | 32 |
| 3' CCN AAR GGC GTY CCC GTY CA 5' | 20 | 32 |

FIG. 2B

```
    CAAGGTCATGTGTCCCAGGAGGAGATAGGGACCGCCCTGCACCACAAACAGC
1   ----+----+----+----+----+----+----+----+----+----+   50
    GTTCCAGTACACAGGGTCCTCCTCTATCCCTGGCGGACGTGGTGTTTGTCG

TCTGCTCCCCTCTTATAAAGTAGGGCAGCCCCTGGAAGCTCCCAGG
51  ----+----+----+----+----+----+----+----+----+----+   100
    AGACGAGGGAGAATATTTCATCCCGTCGGGGACCTTCGAGGGTCC

ATGCCCGGTCCATCTCTCTCTGGCCCTGGTGCTGTCGGCCATGGGGGC
101 ----+----+----+----+----+----+----+----+----+----+   150
    TACGGGCCAGGTAGAGAGAGACCGGGACCACGACAGCCGGTACCCCCG

M  P  G  P  S  L  S  L  A  L  V  L  S  A  M  G  A

TCTGCTGAGGCCAGGGACCCCCAGGGAAGAAGTCTTCAGCACCTCAGCCT
151 ----+----+----+----+----+----+----+----+----+----+   200
    AGACGACTCCGGTCCCTGGGGGTCCCTTCTTCAGAAGTCGTGGAGTCGGA

L  L  R  P  G  T  P  R  E  E  V  F  S  T  S  A  L

TGCCCAGGGAGCAGGCCACAGGCCACTCATCTTTCAGCAAGCC
201 ----+----+----+----+----+----+----+----+----+----+   250
    ACGGGTCCCTCGTGTCCGGTGTCCGGTGAGTAGAAAGTCGTTCGG

```
251 TGGGACTGGCCACTCTCCAGTCTCTGGCTGCCAGGCAGCCCTCTGGACCC
    ----+----+----+----+----+----+----+----+----+----+ 300
    ACCCTGACCGGTGAGAGGTCAGAGACCGACGGTCCGTCGGGAGACCTGGG

W  D  W  P  L  S  S  L  W  L  P  G  S  P  L  D  P

301 CCTGTGCCTGGTGACCCTGCATGGGAGTGGCAACGGGAGCAGGGCCCCC
    ----+----+----+----+----+----+----+----+----+----+ 350
    GGACACGGACCACTGGGACGTACCCTCACCGTTGCCCTCGTCCCGGGGGG

L  C  L  V  T  L  H  G  S  G  N  G  S  R  A  P  L

351 TGCGGGTGGTGGGGGTCCTGAGCAGCTACGAGCAGGCCTTCCTGGAGGCT
    ----+----+----+----+----+----+----+----+----+----+ 400
    ACGCCCACCACCCCCAGGACTCGTCGATGCTCGTCCGGAAGGACCTCCGA

R  V  G  V  L  S  S  Y  E  Q  A  F  L  E  A

401 GTGCGGCGCACCCACTGGGGCCTGAGTGACTTGACCACCTTCGCAGTGTG
    ----+----+----+----+----+----+----+----+----+----+ 450
    CACGCCGCGTGGGTGACCCCGGACTCACTGAACTGGTGGAAGCGTCACAC

V  R  R  T  H  W  G  L  S  D  L  T  T  F  A  V  C

451 CCCCGCTGGCAACGGGCAGCCTGTGCTGCCCCACCTGCAGGGCTGCAGG
    ----+----+----+----+----+----+----+----+----+----+ 500
    GGGGCGACCGTTGCCCGTCGGACACGACGGGGTGGACGTCGCCGACGTCC

```
       CATGGCTGGGGGGAGCCCGGGGGGCGGGTGGTCCTGTGGTCCTGCACCTGGAG
501    ---------+---------+---------+---------+---------+   550
       GTACCGACCCCCCTCGGGCCCCCCGCCCACCAGGACACCAGGACGTGGACCTC

W  L  G  E  P  G  G  R  W  L  V  V  L  H  L  E

GAAGTGACGTGGGAGCCAACACCCCTTGCTGAGGTTCCAGGAGCCTCCGCC
551    ---------+---------+---------+---------+---------+   600
       CTTCACTGCACCCTCGGTTGTGGGAACGACTCCAAGGTCCTCGGAGGCGG

E  V  T  W  E  P  T  P  L  L  R  F  Q  E  P  P  P

TGGAGGAGCCAGCCCCCCAGAGCTGGCCCTGCTGGTGGTGTACCCAGGGC
601    ---------+---------+---------+---------+---------+   650
       ACCTCCTCGGTCGGGGGGTCTCGACCGGGACGACCACCACATGGGTCCCG

G  G  A  S  P  P  E  L  A  L  L  V  V  Y  P  G  P

CTGGCCTGGAGGTCACTGTCACCGGGGCTGGGCTACCTGGCACCCAGAGC
651    ---------+---------+---------+---------+---------+   700
       GACCGGACCTCCAGTGACAGTGGCCCCGACCCGATGGACCGTGGGTCTCG

G  L  E  V  T  V  T  G  A  G  L  P  G  T  Q  S

CTCTGCCTGACCGCGGACTTCCTGGCCCTTGGTCGTGGACCACCC
701    ---------+---------+---------+---------+---------+   750
       GAGACGGACTGGCGCCTGAAGGACCGGAACCAGCACCTGGTGGG

```
751 GGAGGGGGCCTTGGCGCCGGCCCTGGGTTAGCCCCTTACCCTGCGGCCGTG  800
    -------+---------+---------+---------+---------+
    CCTCCCCCGGAACCGCGGCCCGGACCCAATCGGGAATGGGACGCCGGCAC
     E  G  A  W  R  R  P  G  L  A  L  T  L  R  R  R  G

801 GAAATGGTGCGCTCCTGAGCACTGCCCAGTGCTGCAGGGCGCTGCTGTTCGGT  850
    -------+---------+---------+---------+---------+
    CTTTACCACGCGAGGACTCGTGACGGGTCGACGTCCCGACGACAAGCCA
     N  G  A  L  L  S  T  A  Q  L  Q  A  L  L  F  G

851 GCGGACTCCCGCTGCTTCACACGAAAGACCCCAGCCCTGTTACTCTTGCT  900
    -------+---------+---------+---------+---------+
    CGCCTGAGGGCGACGAAGTGTGCTTTCTGGGGTCGGGACAATGAGAACGA
     A  D  S  R  C  F  T  R  K  T  P  A  L  L  L  L

901 GCCGGCCCGGTCTTCGGCACCGATGCCCGCACGGTCGGCTGGACTTGG  950
    -------+---------+---------+---------+---------+
    CGGCCGGGCCAGAAGCCGTGGCTACGGGCGTGCCAGCCGACCTGAACC
     P  A  R  S  S  A  P  M  P  A  H  G  R  L  D  L  V

951 TGCCCTTCCCGCAGCCCAGGGCTTCCCCGAGCAGGAGGCACCGCCC  1000
    -------+---------+---------+---------+---------+
    ACGGGAAGGGCGTCGGGTCCCGAAGGGGCTCGTCCTCCGTGGCGGG
     P  F  P  Q  P  R  A  S  P  E  P  E  E  A  P  P
```

FIG. 3D

```
1001  AGCGCTGATCCCTTCCTGGAGACTCTCACGCGCTGGTGCGCGCTTGC
      ----+----|----+----|----+----|----+----|----+----|----+  1050
      TCGCGACTAGGGAAGGACCTCTGAGAGTGCGCCACCGCGCGAACG
       S   A   D   P   F   L   E   T   L   T   R   L   V   R   A   L   A

1051  GGGACCCCCGGCCCGAGCCTCGCCGGGCTGGCCTTGGACCCGGGGCG
      ----+----|----+----|----+----|----+----|----+----|----+  1100
      CCCTGGGGGCCGGGCTCGGAGCGGCCCGACCGGAACCTGGGCCCGC
       G   P   P   A   R   A   S   P   P   R   L   A   L   D   P   G   A

1101  CACTGGCCTGGTTTCCCGCAGGGTCAACCTGTCGGACCCCGCGGCC
      ----+----|----+----|----+----|----+----|----+----|----+  1150
      GTGACCGGACCAAAGGGCGTCCCAGTTGGACAGCCTGGGGCGCCGG
       L   A   G   F   P   Q   G   Q   V   N   L   S   D   P   A   A

1151  CTGGAGCGGCCTGCTGGACGGCGAGGAGCCCCTGCTGCTGCTGCCGCC
      ----+----|----+----|----+----|----+----|----+----|----+  1200
      GACCTCGCGGACGACCTGCCGCTCCTCGGCGACGACGACGACGGCGG
       L   E   R   L   L   D   G   E   E   P   L   L   L   L   P   P

1201  GACGGCAGCCACCACCGGGGTCCCCGCAACGCGCAAGGTCCCAAGTCCC
      ----+----|----+----|----+----|----+----|----+----|----+  1250
      CTGCCGTCGGTGGTGGCCCCAGGGGCGTTGCGCGTTCCAGGGTTCAGGG
       T   A   T   T   G   V   P   A   T   P   Q   G   P   K   S   P
```

FIG. 3E

```
          CTCTGTGGGCCGGGGACTAGCGGCCGGGTGGCTGCCGAGCTTCAGGCG
1251      ---------+---------+---------+---------+---------+  1300
          GAGACACCCGGCCCCTGATCGCGGCCCACCGACGGCTCGAAGTCCGC

L   W   A   A   G   L   A   R   R   V   A   E   L   Q   A

GTGGCCGCCGAGCTGCGTGCCCTCCCGGGGCTGCCTCCAGCTGCCCCACC
1301      ---------+---------+---------+---------+---------+  1350
          CACCGGCGGCTCGACGCACGGGAGGGCCCCGACGGAGGTCGACGGGGTGG

V   A   E   L   R   A   L   P   G   L   P   P   A   A   P   P

GCTGCTGGGCCGGCCTGCTGGCACTGTGCCCGGGAAACCCAGACAGCCCCG
1351      ---------+---------+---------+---------+---------+  1400
          CGACGACCCGGCCGGACGACCGTGACACGGGCCCTTTGGGTCTGTCGGGGC

L   L   A   R   L   L   A   L   C   P   G   N   P   D   S   P   G

GCGGCCCCGCTGCGCGCTGCTGCTGCTCAAAGCGCTGCAGGGCCTGCGC
1401      ---------+---------+---------+---------+---------+  1450
          CGCCGGGGCGACGCGCGACGACGACGAGTTTCGCGACGTCCCGGACGCG

G   P   L   R   A   L   L   L   K   A   L   Q   G   L   R

GCTGAGTGGGGCGGGGGAGGCGGAGCCTCTGCACGGGCGGCAGGCAG
1451      ---------+---------+---------+---------+---------+  1500
          CGACTCACCGGCGCCCTCGCCCCTCGAGACGTGCCCGCCGTCGCGTC

```
1501  CGCCGGGGCCGGGGCTGCAGAGACGGGCCGTGCGCTCTGCGTGAGCTGAGCG
      ----+----+----+----+----+----+----+----+----+----+  1550
      GCGGCCCCGGCCGACGTCTGCCCGGCACGCGAGACGCACTCGACTCGC
       A  G  A  A  A  A  D  G  P  C  A  L  R  E  L  S  V

1551  TAGACCCTGCGGGCCGAGGCGCTCGGTGCTCATCCCCGAGACATACCAGGCC
      ----+----+----+----+----+----+----+----+----+----+  1600
      ATCTGGGACGCCCCGGCTCGCGAGCCACGAGTAGGGGCTCTGTATGGTCCGG
       D  L  R  A  E  R  S  V  L  I  P  E  T  Y  Q  A

1601  AACAACTGCCAGGGGGCCTGCGGCCTCAGTCGGACCGCAACCCGCG
      ----+----+----+----+----+----+----+----+----+----+  1650
      TTGTTGACGGTCCCCCGGACCGCCGGAGTCAGCAGCCTGGCGTTGGGCGC
       N  N  C  Q  G  A  C  G  W  P  Q  S  D  R  N  P  R

1651  CTACGGGCAACCACGTGGTGCTGCTAAAGATGCAGGCCCGGGCGCCA
      ----+----+----+----+----+----+----+----+----+----+  1700
      GATGCCGTTGGTGCACCACGACGATTTCTACGTCCGGGCCGCGGGT
       Y  G  N  H  V  V  L  L  K  M  Q  A  R  G  A  T

1701  CCCTGGCGCGCCCCGCCCTGCGTGTGCCCACAGCCTACACCGGCAAGCTC
      ----+----+----+----+----+----+----+----+----+----+  1750
      GGGACCGCGCGGGGCGGGACGACACACGGGTGTCGGATGTGGCCGTTCGAG
       L  A  R  P  P  C  C  V  P  T  A  Y  T  G  K  L
```

FIG. 3G

```
1751  CTCATCAGCCTGTCCGAGGAGCGGCATCAGTGCGCACCACGTCCCAAACAT
      -------+---------+---------+---------+---------+--  1800
      GAGTAGTCGGACAGGCTCCTCGCGTAGTCACGCGTGGTGCAGGGTTTGTA
       L  I  S  L  S  E  E  R  I  S  A  H  H  V  P  N  M

1801  GGTGGCCACCGAATGCGGCCGGTGACCCTCGCGCCGTGCTCCTCGTGC
      -------+---------+---------+---------+---------+--  1850
      CCACCGGTGGCTTACGCCGGCCACTGGGAGCGCGGCACGAGGAGCACG
       V  A  T  E  C  G  C  R

1851  TGCCCCGGCCCCGTATTTATTCGGACCCCGTCATTGCCCCATTAAACACGG
      -------+---------+---------+---------+---------+--  1900
      ACGGGGCCGGGGCATAAATAAGCCTGGGGCAGTAACGGGGTAATTTGTGCC

1901  GAAGGC
      ------  1906
      CTTCCG
```

FIG. 3H

```
     AAGGTCGCGGGCAGAGGAGATAGGGGTCTGTCCTGCACAAACACCCCACCT
1    --------+---------+---------+---------+---------+  50
     TTCCAGCGCCCGTCTCTCCTCTATCCCCAGACAGGACGTGTTTGTGGGGTGGA

TCCACTCGGCTCACTTAAGGCAGGCAGCCCCTGGCAGCACCCACG
51   --------+---------+---------+---------+---------+  100
     AGGTGAGCCGAGTGAATTCCGTCCGTCGGGACCCGTCGTGGGTGC

ATGCGGGACCCTGCCTCTCACCAGCCTGGCCCTAGTGCTGTCTGCCCTGGG
101  --------+---------+---------+---------+---------+  150
     TACGCCCTGGACGGAGAGTGGTCGGACCGGGATCACGACAGACGGGACCC

M  R  D  L  P  L  T  S  L  A  L  V  L  S  A  L  G

GGCTCTGCTGGGGACTGAGGCCCTCAGAGCAGAGGAGCCAGCTGTGGGCA
151  --------+---------+---------+---------+---------+  200
     CCGAGACGACCCCTGACTCCGGGAGTCTCGTCTCCTCGGTCGACACCCGT

A  L  L  G  T  E  A  L  R  A  E  E  P  A  V  G  T

CCAGTGGCCCTCATCTTTCCGAGAAGACTTGGACTGGCCTCCAGGCATCCCA
201  --------+---------+---------+---------+---------+  250
     GGTCACCGGGAGTAGAAAGGCTCTTCTGAACCTGACCGGAGGTCCGTAGGGT

```
251  CAAGAGCCTCTGTGCCTGGTGGCACTGGGGGACAGCAATGGCAGCAG
     ----+----|----+----|----+----|----+----|----+----  300
     GTTCTCGGAGACACGGACCACCGTGACCCCCTGTCGTTACCGTCGTC

Q  E  P  L  C  L  V  A  L  G  G  D  S  N  G  S  S

301  CTCCCCCCTGCGGGTGGTGGGGGCTCTAAGCGCCTATGAGCAGGCCTTCC
     ----+----|----+----|----+----|----+----|----+----  350
     GAGGGGGGACGCCCACCACCCCCGAGATTCGCGGATACTCGTCCGGAAGG

S  P  L  R  V  V  G  A  L  S  A  Y  E  Q  A  F  L

351  TGGGGGCCGTGCAGAGGGCCCGCTGGGGCCCCGAGACCTGGCCACCTTC
     ----+----|----+----|----+----|----+----|----+----  400
     ACCCCCGGCACGTCTCCCGGGCGACCCCGGGGCTCTGGACCGGTGGAAG

G  A  V  Q  R  A  R  W  G  P  R  D  L  A  T  F

401  GGGGTCTGCAACACCGGTGACAGGCAGGCTGCCCTTGCCCTCTCTACGGCG
     ----+----|----+----|----+----|----+----|----+----  450
     CCCCAGACGTTGTGGCCACTGTCCGTCCGACGGGAACGGGAGAGATGCCGC

G  V  C  N  T  G  D  R  Q  A  A  L  P  S  L  R  R

451  GCTGGGGGCCTGGCTGCGCGACCCCTGGGGACCCCGTGCGGACCACCAGGATG
     ----+----|----+----|----+----|----+----|----+----  500
     CGACCCCCGGACCGACGCGCTGGGGACCCCTGGGGCACGCCTGGTGGTCCTAC

```
501  ACCTGGAGGAAGGTATGTGGGCCCAGCCCCAAGCTTGGCACCGCCGTCT
     ----+---------+---------+---------+---------+  550
     TGGACCTCCTTCCATACACCCCGGGTCGGGGTTCGAACCGTGGCGGCAGA
         L  E  E

551  TCCTTCAGGTGGGGCCCGGGTCCTCCTAGGGAAGATCAGGGCTGGCAGAGC
     ----+---------+---------+---------+---------+  600
     AGGAAGTCCACCCCGGGCCCAGGAGGATCCCTTCTAGTCCCGACCGTCTCG

601  CCCCACCCCTGGGGCAGGAGGCTGTGGTCTCTTGTTCCTAGGACTGGGTTGCG
     ----+---------+---------+---------+---------+  650
     GGGGTGGGGACCCCGTCCCTCCGACACCAGAACAAGGATCCTGACCCAACGC

651  GGTCCGTGGCCTGGAAGGTGGGCACCACACTCTGTCCTGTCCCCGAAGCC
     ----+---------+---------+---------+---------+  700
     CCAGGCACCGGACCTTCCACCCGTGGTGTGAGACAGGACAGGGCTTCGG

701  CAGCTCTCTTAGACTTGCCCCTGCCTCGGTGCCTGCCAGGGAGAGAGCTGCTGCCT
     ----+---------+---------+---------+---------+  750
     GTCGAGAATCTGAACGGGACGGAGCCACGGTCCCCTCTCTCGACGACGGA
```

```
751 TCTCCCCACCCCCTGAAGACGACGCAGGGCTCGGGGCCAGTGGAACCCTTC
    ---------+---------+---------+---------+---------+ 800
    AGAGGGGTGGGGACTTCTGCTGCGTCCCGAGCCCCGGTCACCTTGGGAAG

801 TTCCCACAGCCCCCAGCCTGTTCTCAGGCCTGGCCGCTAAGATACTCCCT
    ---------+---------+---------+---------+---------+ 850
    AAGGGTGTCGGGGTCGGACAAGAGTCCCGGCGACCGGATTCTATGAGGGA

851 GCGGGGAAGGGGCTTCATCGGGCACCCAACCCCAGAGACCCCAGGCGGC
    ---------+---------+---------+---------+---------+ 900
    CGCCCCTTCCCCGAAGTAGCCCGTGGGGTTGGGGTCTCTGGGGTCCCCGCCG

901 AGCCCCACCCCACAGCCCTCAGACGCAGCCCTGCCCCTGCCCCGTCACC
    ---------+---------+---------+---------+---------+ 950
    TCGGGGTGGGGTGTCGGAGTCTGCGTCGGGACGGGGACGGGGACGGCAGTGG

951 GCTCCCTGGCTGCAGGAAGGCAGCTAAGAGAGGGGCACCCTTTGTCCCCGCT
    ---------+---------+---------+---------+---------+ 1000
    CGAGGGACCGACGTCCTTCCGTCGATTCTCTCCCCGTGGGAACAGGGGGCGA
```

FIG. 6D

```
1001  TGAGGTCCCCTGCACAGTGGCCAGAGCGGCAGGGACAGATCCCAAAGATT
      ----+----|----+----|----+----|----+----|----+----  1050
      ACTCCAGGGGACGTGTCACCGGTCTCGCCGTCCCTGTCTAGGGTTTCTAA

1051  CCCGGGGGGTGTGGCCTTCAATGGCTCAGGCGTCCCCTGCTCCCGGCT
      ----+----|----+----|----+----|----+----|----+----  1100
      GGGCCCCCCACACCGGAAGTTACCGAGTCCGCAGGGACGACAGGGCCGA

1101  GCAGTGACCTGGGAGCCAACACCCTCGCTGAGGTTCCAGGAGCCCCGCC
      ----+----|----+----|----+----|----+----|----+----  1150
      CGTCACTGGACCCTCGGTTGTGGGAGCGACTCCAAGGTCCTCGGGGCGG
          V   T   W   E   P   T   P   S   L   R   F   Q   E   P   P   P

1151  TGGAGGAGCTGGCCCCCAGAGCTGGGCTGCTGGTGCTGTACCCTGGGC
      ----+----|----+----|----+----|----+----|----+----  1200
      ACCTCCTCGACCGGGGGTCTCGACCCGACGACCACGACATGGGACCCG
          G   G   A   G   P   P   E   L   A   L   L   V   L   Y   P   G   P

1201  CTGGCCCTGAGGTCACTGTGACGAGGGCTGGGGTGCCCAGGTA
      ----+----|----+----|----+----|----+----|----+----  1250
      GACCGGGACTCCAGTGACACTGCTCCCGACCCCACGGGTCCAT
          G   P   E   V   T   V   T   R   A   G   L   P   G   A   Q
```

```
1251  CCAGGGAGTTGCATGGGGCCCGGGTGCCGGGGGCATGAATT  1300
      ----+----+----+----+----+----+----+----+
      GGTCCCTCAACGTACCCCGGGCCACGGCCCCCGTACTTAA

1301  TGTTGCAGGGTCTGCAGTACTGAGAACAGCGTAGAACCAGTGGGCGATGGG  1350
      ----+----+----+----+----+----+----+----+----+----+
      ACAACGTCCCAGACGTCATGACTCTTGTCGCATCTTGGTCACCGCTACCC

1351  AGGAAGGGGACCGGTAGAGCGGGCTGGGTAAGCCTCCATCCAGCCGGGC  1400
      ----+----+----+----+----+----+----+----+----+---+
      TCCTTCCCCTGGCCATCTCGCCCGACCCATTCGGAGGTAGGTCGGCCCG

1401  TGAGCCCCTGGTCTCTCCGCAGAGCCTCTGCCCCTCCCGAGACACCCGCTACC  1450
      ----+----+----+----+----+----+----+----+----+----+
      ACTCGGGACCAGAGAGGCGTCTCGGAGACGGGAGGGCTCTGTGGGCGATGG
          S   L   C   P   S   R   D   T   R   Y   L

1451  TGGTGTTAGCGGTGGACCGGCCCTGCGCCCTGGGCGGGCTCCGGGCTG  1500
      ----+----+----+----+----+----+----+----+----+---+
      ACCACAATCGCCACCTGGCCGGGACGCGGGACCCGCCGGAGGCCCGAC
       V   L   A   V   D   R   P   A   G   A   W   R   G   S   G   L
```

```
                     GCCTTGACCCTGCAGCCCCGCGGAGAGGGTAGGTCCGCGTGGAGAGGGAC
1501      -----+---------+---------+---------+---------+---------+  1550
                     CGGAACTGGGACGTCGGGGCGCCTCTCCCATCCAGGCGCACCTCTCCCTG

A  L  T  L  Q  P  R  G  E

GGGGAGCCGGGTCGACTGCCCCCCAGCCCCTGAGCCAGCCGCG
1551      -----+---------+---------+---------+---------+---------+  1600
                     CCCCTCGGCCCAGCTGACGGGGGGTCGGGGACTCGGTCGGCGC

TGCCCACCACCGACAGACTCCCGGCTGAGTACCGCCTGCAGGCACT
1601      -----+---------+---------+---------+---------+---------+  1650
                     ACGGGGTGGTGGCTGTCTGAGGGCCGACTCATGGCGGACGTCCGTGA

D  S  R  L  S  T  A  R  L  Q  A  L

GCTGTTCGGCGACGACCACCGCTGCTTCACACGGATGACCCCGGCCCTGC
1651      -----+---------+---------+---------+---------+---------+  1700
                     CGACAAGCCGCTGCTGGTGGCGACGAAGTGTGCCTACTGGGGCCGGGACG

L  F  G  D  D  H  R  C  F  T  R  M  T  P  A  L  L

TCCTGCTGCCGGGTCCGAGCCCGCCTGCCGCACGGCCAGCTG
1701      -----+---------+---------+---------+---------+---------+  1750
                     AGGACGACGGCCCAGGCTCGGGCGGACGGCGTGCCGGTCGAC

```
1751  GACACCGTGCCCTTCCCGCCGCCCAGGTGCGGCAGGCACCGGGACACGG   1800
      ----------+---------+---------+---------+---------+
      CTGTGGCACGGGAAGGGCGGCGGGTCCACGCCGTCCGTGGCCCTGTGCC

D  T  V  P  F  P  P  P  R

1801  GGCAGGAGCGGGCGGGGCGGCCGTGGCCGCTCGTGGCCTCTCAACTCCTC   1850
      ----------+---------+---------+---------+---------+
      CCGTCCTCGCCCGCCCCGCCGGCACCGGCGAGCACCGGAGAGTTGAGGAG

1851  CAATTGCGGGTTCCAGGCCATCCGGGAACTCGAGGAGTCGCCACCCAGC   1900
      ----------+---------+---------+---------+---------+
      GTTAACGCCCAAGGTCCGGTAGGCCCTTGAGCTCCTCAGCGGTGGGTCG

P  S  A  E  L  E  E  S  P  P  S

1901  GCAGACCCCTTCCTGGAGACGCTCACGCGCCTGGTGCGGGCTGCGGGT   1950
      ----------+---------+---------+---------+---------+
      CGTCTGGGGAAGGACCTCTGCGAGTGCGCGGACCACGCCCGACGCCCA

A  D  P  F  L  E  T  L  T  R  L  V  R  A  L  R  V

1951  CCCCCCGGCCCCGGGCCTCCGCGCCTGGCCCTGGATCCGGACGCGC   2000
      ----------+---------+---------+---------+---------+
      GGGGGGCCGGGGCCCGGAGGCGCGGACCGGGACCTAGGCCTGCGCG

```
2001  TGGCCGGCTTCCCCGCAGGGCCTAGTCAACCTGTCGGACCCCGGGGCTG
      ----------+---------+---------+---------+--------- 2050
      ACCGGCCGAAGGGCGTCCCGGATCAGTTGGACAGCCTGGGGCCGCGAC

A  G  F  P  Q  G  L  V  N  L  S  D  P  A  A  L

2051  GAGCGCCTACTCGACGGGCGAGGAGCCGTGCTGCTGCTGCTGAGGCCCAC
      ----------+---------+---------+---------+--------- 2100
      CTCGCGGATGAGCTGCCCGCTCCTCGGCACGACGACGACGACTCCGGGTG

E  R  L  L  D  G  E  E  P  L  L  L  L  R  P  T

2101  TGCGGCCACCACCGGGGATCCTGCCCCTGCACGACCCCACGTCGGCGC
      ----------+---------+---------+---------+--------- 2150
      ACGCCGGTGGTGGCCCCTAGGACGGGGACGTGCTGGGGTGCAGCCGCG

A  A  I  T  G  D  P  A  P  L  H  D  P  T  S  A  P

2151  CGTGGGCCACGGCCCTGGCGCGCCGCGTGGCTGAACTGCAAGGCGG
      ----------+---------+---------+---------+--------- 2200
      GCACCCGGTGCCGGGACGCGCGGCGGCACCGACTTGACGTTCGCCGC

W  A  T  A  L  A  R  R  V  A  A  E  L  Q  A  A

2201  GCTGCCGAGCTGCGAAGCCTCCGGGTCTGCCTCCGGCCACAGCCCCGCT
      ----------+---------+---------+---------+--------- 2250
      CGACGGCTCGACGCTTCGGAGGCCCAGACGGAGGCCGGTGTCGGGGCGA

```
2251 GCTGGGCGCCTGCTCGCGCTCTGCCCAGGAGGCCCCGGCGGGCCTCGGCG
     ---------+---------+---------+---------+---------+ 2300
     CGACCCGCGGACGAGCGCGAGACGGGTCCTCCGGGGCCGCCGGAGCCGC

L  A  R  L  L  A  L  C  P  G  G  P  G  G  L  G  D

2301 ATCCCCTGCGAGGCGTGCTGTCTCCTGAAGGCGCTGCAGGGCCTGCGCGTG
     ---------+---------+---------+---------+---------+ 2350
     TAGGGGACGCTCGCGACGACGAGGACTTCCGCGACGTCCCGGACGCGCAC

P  L  R  A  L  L  L  K  A  L  Q  G  L  R  V

2351 GAGTGGCGCGGGATCCGCGGGCCGGGTCGGGCCGGTCGGGGCACAGCGCAGCGC
     ---------+---------+---------+---------+---------+ 2400
     CTCACCGCGCCCTAGGCGCCCGGCCCAGCCCGGCCAGCCCGTGTCGCGTCGCG

E  W  R  G  R  D  P  R  G  P  G  R  A  Q  R  S  A

2401 GGGGGCCACCGCCGCCGACGGGCCGTGCGCGCTGCGCGAGCTCAGCGTAG
     ---------+---------+---------+---------+---------+ 2450
     CCCCCGGTGGCGGCGGCTGCCCGGCACGCGCGACGCGCTCGAGTCGCATC

G  A  T  A  A  D  G  P  C  A  L  R  E  L  S  V  D

2451 ACCTCCGCGCCGAGCGCTCCGTACTCATCCCCGAGACCTACCAGGCCAAC
     ---------+---------+---------+---------+---------+ 2500
     TGGAGGCGCGGCTCGCGAGGCATGAGTAGGGGCTCTGGATGGTCCGGTTG

L  R  A  E  R  S  V  L  I  P  E  T  Y  Q  A  N

2501 AATTGCCAGGGCGTGTGCGGCTGGCCTCAGTCCGACCGCAACCCGCGCTA
     ---------+---------+---------+---------+---------+ 2551
     TTAACGGTCCCGCACACGCCGACCGGAGTCAGGCTGGCGTTGGGCGCGAT

```
2551  CGGCAACCACGTGGTGCTGCTGAAGATGCAGGCCCGTGGGGCCGCCC       2600
      ----+----+----+----+----+----+----+----+----+----
      GCCGTTGGTGCACCACGACGACTTCTACGTCCGGGCACCCCGGCGGG

G   N   H   V   V   L   L   K   M   Q   A   R   G   A   A   L

2601  TGGGCGGCCCACCCTGTGCCGTGCCCACCGCGGGCAAGCTGCTC         2650
      ----+----+----+----+----+----+----+----+----+----
      ACCGCGGGGTGGGACGACGACGGGTGGCGGATGCGCCGTTCGACGAG

A   R   P   P   C   C   V   P   T   A   Y   A   G   K   L   L

2651  ATCAGCCTGTCGGAGGAACGCATCAGCGCGCACCACGTGCCCAACATGGT    2700
      ----+----+----+----+----+----+----+----+----+----
      TAGTCGGACAGCCTCCTTGCGTAGTCGCGCGTGGTGCACGGGTTGTACCA

I   S   L   S   E   E   R   I   S   A   H   H   V   P   N   M   V

2701  GGCCACCGAGTGTGGCTGCCGGTGACCCCTGCGCCGCGGACTCCTGCC     2750
      ----+----+----+----+----+----+----+----+----+----
      CCGGTGGCTCACACCGACGGCCACTGGGGACGCGGCGCCTGAGGACGG

A   T   E   C   G   C   R

2751  CCGAGGGTCCGGGACGGCCGCCCCAGCTCGCGCCCCTTCCCATATTTATTCGG  2800
      ----+----+----+----+----+----+----+----+----+----
      GGCTCCCAGGCCTGCCGGGGTCGAGCGCGGGGAAGGGTATAAATAAGCC

2801  ACCCCAAGCATCGCCCCAATAAAGACCAGCAAGC         2834
      ----+----+----+----+----
      TGGGGTTCGTAGCGGGGTTATTTCTGGTCGTTCG
```

FIG. 6K

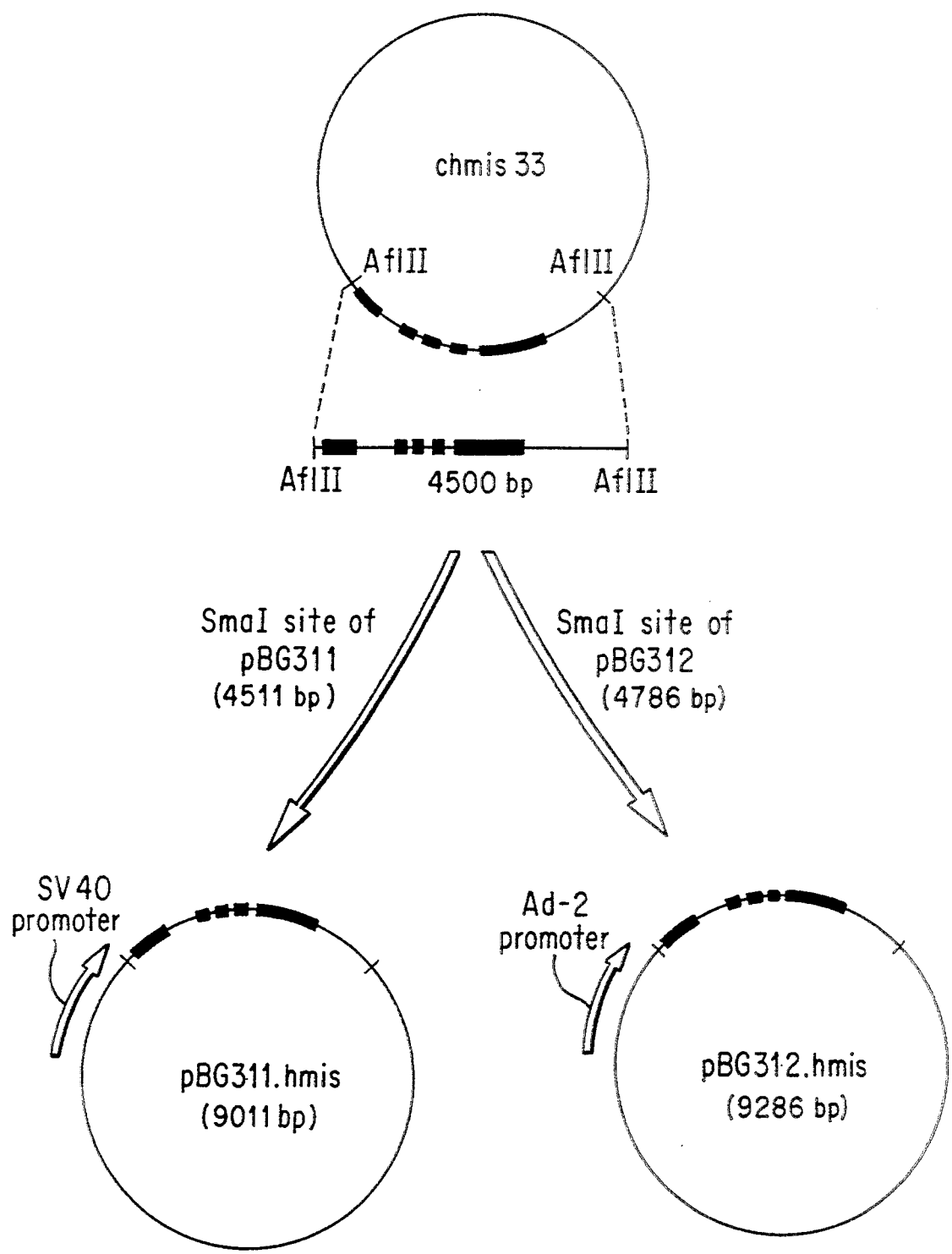
F I G. 7

COMPOSITION COMPRISING MULLERIAN INHIBITING SUBSTANCE-LIKE POLYPEPTIDES

This invention was supported by United State Federal Government funding. The Federal Government has certain in the invention.

This application is a continuation of application Ser. No. 07/693,764, filed Apr. 25, 1991, now abandoned, which is a continuation of 06/923,879, filed Oct. 28, 1986, now abandoned, which is a continuation-in-part of 06/792,880, now U.S. Pat. No. 5,047,336, filed Oct. 30, 1985.

This invention relates to DNA sequences, recombinant DNA molecules and processes for producing Mullerian Inhibiting Substance (MIS)-like polypeptides. More particularly, the invention relates to DNA sequences and recombinant DNA molecules that are characterized in that they code for at least one MIS-like polypeptide. Accordingly, hosts transformed with these sequences may be employed in the processes of this invention to produce the MIS-like polypeptides of this invention. These polypeptides possess anti-tumor activity and are useful in the treatment of cancer, especially cancer of the female genital tract (e.g., ovarian cancer).

The production of at least two testicular factors by the male gonad shortly after differentiation was first postulated to be necessary for normal male reproductive development following the fetal rabbit castration experiments of Jost (*C. R. Soc. Biol.*, 140, 463–64 (1946) and *C. R. Soc. Biol.*, 141, 135–36 (1947)). One factor, testosterone, was shown to be responsible for differentiation of the epididymis, vas deferens, and seminal vesicles from the Wolffjan ducts. Virilization of the male was not complete, however, unless a second, nonsteroidal, factor was present to stimulate regression of the Mullerian ducts, the anlagen of the female reproductive system. Jost later named this second regulatory factor Mullerian Inhibiting Substance (MIS) (*Rec. Prog. Horm. Res.*, 8, 379–418 (1953)). Interest in purifying MIS was heightened by the finding that bovine MIS in addition to its important role in development, was cytotoxic to the human ovarian tumor cell line HOC-21 both in vitro (Donahoe et al., *Science*, 205, 913–15 (1979); and Fuller et al., *J. Clin. Endocrinol. Metab.*, 54, 1051–55 (1982)) and in vivo in a nude mouse model (Donahoe et al., *Ann. Surg.*, 194, 472–80 (1981)). Highly purified fractions of bovine MIS also inhibit colony growth of primary ovarian and endometrial cancers derived from patients (Fuller et al., *Gyn. Oncol.* (1985)).

A variety of approaches have been used to attempt the purification of MIS (for reviews see Josso et al., *Rec. Prog. Hom. Res.*, 33, 117–67 (1977) and Donahoe et al., *Rec. Prog. Hom. Res.*, 38, 279–330 (1982)). Newborn calf testes contain a high level of MIS up to 8 weeks after birth (Donahoe et al., *Biol. Reprod.*, 16, 238–43 (1977)), providing an accessible tissue source for biochemical purification. Donahoe and coworkers originally obtained active;, crude MIS preparations of calf testes by incubation with guanidine hydrochloride in the presence of a protease inhibitor (Swarm et al., *Dev. Biol.*, 69, 73–84 (1979)). Subsequent fractionation by ion exchange or gel filtration chromatography enhanced purity about thirty-fold. Similar results were obtained by others working with incubation medium from fetal calf testes (Picard et al., *Biomedicine* 25, 147–50 (1976), and Josso et al. *Rec. Prog. Hom. Res.*, 33, 117–67 (1977)). The purity of bovine MIS was further enhanced when sequential ion exchange chromatography was coupled with sequential lectin affinity chromatography (Budzik et al., *Cell* 21, 909–15 (1980); U.S. Pat. Nos. 4,404,188; and 4,510,131). The results of Budzik et al. (supra) suggested that bovine MIS was a large molecular weight glycoprotein and provided semipurified MIS fractions that were used to prepare anti-MIS monoclonal antibodies (Mudgett-Hunter et al., *J. Immunol.*, 128, 1327–33 (1982); Shima et al., *Hybridoma*, 3, 201–14 (1984); and U.S. Pat. No. 4,487,833). Lectin-affinity-purified bovine MIS fractionated by gel filtration under native conditions exhibited a single peak at approximately 200,000 daltons, although on denaturing polyacrylamide gels, this fraction contained multiple components suggesting a multiple subunit structure (Budzik et al., *Cell*, 21, 909–15 (1980)).

Subsequently, Matrix Gel Green A was used to achieve greater than 2000-fold purification of bovine MIS with a concomitant 60% recovery of starting activity. This was achieved by stabilizing MIS activity with the dialyzable protecting agents 2-mercaptoethanol, EDTA, and Nonidet-P40(NP40). Analysis of the 2000-fold-purified MIS fraction by SDS-polyacrylamide gel electrophoresis indicated that only one component, migrating at 140,000 daltons was sensitive to reduction, although a number of other moieties were detected. Reduction of the sample prior to electrophoresis showed a new band at 74,000 daltons with the simultaneous loss of the 140,000 dalton species,, while the migrations of all other components in this fraction were effectively unchanged (Budzik et al., *Cell*, 34, 307–14 (1983)). This is consistent with the suggestion that bovine MIS is a dimer of disulfide-linked subunits with a total molecular weight of 124,000 daltons (Picard et al., *Mol. Cell. Endocrinol.*, 12, 17–30 (1978)).

MIS of greater purity and in large amounts is urgently needed for oncological studies because the present methods of treating cancers of the female genital tract are not adequate. Cancers of the female genital tract represent approximately 9 percent of all cancers in humans. Currently, physicians use surgery and radiation when genital tract cancers are detected in early stages (for example, ovarian carcinoma Stage I–IIa). Although these methods of treatment are effective, they render the patients sterile. Chemotherapy is used in advanced cases (Stage III–IV) when patients are classified as inoperable. Of the chemotherapeutic agents, cisplatinum, adriamycin and cytoxan are the most commonly used. These drugs have proven to be most effective when combined in cisplatinum containing regimens and used on a long-term basis. Each of these drugs is considered to be highly toxic and their use requires intermittent hospitalization of the patients.

MIS, as a natural biological regressor, is expected to have less side effects because of its specificity. Other potential uses of MIS include the treatment of tumors with high levels of epithelial growth factor (EGF) receptors (Hutson et al., *Science*, 223, 586–89 (1984)), such as those from the head and neck, lung, epithelial lining of the digestive tract, cornea and skin. It is also believed that MIS may inhibit germ cell meiosis since the substance has been localized to the granulosa cell of the Graffian follicle. Thus, its use as a contraceptive agent is being explored. These broader potential applications further increase the importance of providing an adequate source of MIS.

A purification procedure for bovine MIS has been devised by Donahoe and co-workers (Budzik et al., in

*Developmental Mechanisms: Normal and Abnormal*, Lash, J. W., ed. Alan R. Liss, Inc., Scientific, Medical and Scholarly Publications, pages 207–23 (1985)). Using a scaled-up procedure, about 1 mg of 80% pure protein can be isolated from 1000 newborn calf testes. However, this purification process is labor intensive and costly. Most importantly, it does not provide enough material for extensive oncological studies. Recombinant DNA technology would provide a larger source of bovine MIS.

Although most work on MIS has been done on bovine MIS, there is also some interest in chick MIS. It appears from an article in *Chemical Week* (Jan. 30, 1985, page 69), that C. S. Teng claims to have purified chick MIS and isolated the MIS gene from chick embryos. However, no further details were reported.

For clinical use, human MIS is preferred to MIS of animal origin. Human MIS, however, is even more difficult to obtain because human tissue in sufficient quantities is not available; thus, the only way to produce human MIS is through recombinant DNA technology. Accordingly, the isolation of the human gene for MIS was of paramount importance.

The present invention addresses the foregoing problems by providing DNA sequences coding for at least one MIS-like polypeptide, recombinant DNA molecules comprising such sequences, hosts comprising such sequences and processes for producing such polypeptides in hosts transformed with those DNA sequences, and in higher purity than heretofore available.

The DNA sequences of this invention are selected from the group consisting of (a) the DNA sequences

```
AAGGTCGCGGCAGAGGAGATAGGGGTCTGTCCTGCACAAACACCCCACCT
TCCACTCGGCTCACTTAAGGCAGGCAGCCCAGCCCCTGGCAGCACCCACG
ATGCGGGACCTGCCTCTCACCAGCCTGGCCCTAGTGCTGTCTGCCCTGGG
GGCTCTGCTGGGGACTGAGGCCCTCAGAGCAGAGGAGCCAGCTGTGGGCA
CCAGTGGCCTCATCTTCCGAGAAGACTTGGACTGGCCTCCAGGCATCCCA
CAAGAGCCTCTGTGCCTGGTGGCACTGGGCGGGGACAGCAATGGCAGCAG
CTCCCCCCTGCGGGTGGTGGGGGCTCTAAGCGCCTATGAGCAGGCCTTCC
TGGGGGCCGTGCAGAGGGCCCGCTGGGGCCCCCGAGACCTGGCCACCTTC
GGGGTCTGCAACACCGGTGACAGGCAGGCTGCCTTGCCCTCTCTACGGCG
GCTGGGGGCCTGGCTGCGGGACCCTGGGGGGCAGCGCCTGGTGGTCCTAC
ACCTGGAGGAAGGTATGTGGGGCCCAGCCCCAAGCTTGGCACCGCCGTCT
TCCTTCAGGTGGGCCGGGTCCTCCTAGGGAAGATCAGGGGCTGGCAGAGC
CCCCACCCTGGGCAGGGAGGCTGTGGTCTTGTTCCTAGGACTGGGTTGCG
GGTCCGTGGCCTGGAAGGTGGGCACCACACTCTGTCCTGTCCCCGAAGCC
CAGCTCTTAGACTTGCCCCTGCCTCGGTGCCAGGGAGAGAGCTGCTGCCT
TCTCCCCACCCCTGAAGACGACGCAGGGCTCGGGGCCAGTGGAACCCTTC
TTCCCACAGCCCCAGCCTGTTCTCAGGGCCGCTGGCCTAAGATACTCCCT
GCGGGGAAGGGGCTTCATCGGGCACCCCAACCCAGAGACCCCAGGGCGGC
AGCCCCACCCACAGCCTCAGACGCAGCCCCTGCCTGCCCCTGCCGTCACC
GCTCCCTGGCTGCAGGAAGGCAGCTAAGAGGGGCACCCTTGTCCCCCGCT
TGAGGTCCCCTGCACAGTGGCCAGAGCGGCAGGGACAGATCCCAAAGATT
CCCGGGGGGTGTGGCCTTCAATGGCTCAGGCGTCCCCTGCTGTCCCGGCT
GCAGTGACCTGGGAGCCAACACCCTCGCTGAGGTTCCAGGAGCCCCCGCC
TGGAGGAGCTGGCCCCCCAGAGCTGGCGCTGCTGGTGCTGTACCCTGGGC
CTGGCCCTGAGGTCACTGTGACGAGGGCTGGGCTGCCGGGTGCCCAGGTA
CCAGGGAGTTGCATGGGGCAGTGCCCGGGCCGTGGCGGGGGGCATGAATT
TGTTGCAGGGTCTGCAGTACTGAGAACAGCGTAGAACCAGTGGCGATGGG
AGGAAGGGGACCGGTAGAGCGGGCTGGGTAAGCCTCCATCCAGCCGGGC
TGAGCCCTGGTCTCCGCAGAGCCTCTGCCCCTCCCGAGACACCCGCTACC
TGGTGTTAGCGGTGGACCGCCCTGCGGGGGCCTGGCGCGGCTCCGGGCTG
GCCTTGACCCTGCAGCCCCGCGGAGAGGGTAGGTCCGCGTGGAGAGGGAC
GGGGAGCCGGGTCGACTGCCCCCGGGCCCCCAGCCCCTGAGCCAGCCGCG
TGCCCACCCACCGCAGACTCCCGGCTGAGTACCGCCCGGCTGCAGGCACT
GCTGTTCGGCGACGACCACCGCTGCTTCACACGGATGACCCCGGCCCTGC
TCCTGCTGCCGCGGTCCGAGCCCGCGCCGCTGCCTGCGCACGGCCAGCTG
GACACCGTGCCCTTCCCGCCGCCCAGGTGCGCGCAGGCACCGGGACACGG
GGCAGGAGCGGGCGGGGGCGGCGTGGCCTCGTGGCCGCTCTCAACTCCTC
CAATTGCGGGTTCCAGGCCATCCGCGGAACTCGAGGAGTCGCCACCCAGC
GCAGACCCCTTCCTGGAGACGCTCACGCGCCTGGTGCGGGCGCTGCGGGT
CCCCCCGGCCCGGGCCTCCGCGCCGCGCCTGGCCCTGGATCCGGACGCGC
TGGCCGGCTTCCCGCAGGGCCTAGTCAACCTGTCGGACCCCGCGGCGCTG
GAGCGCCTACTCGACGGCGAGGAGCCGCTGCTGCTGCTGAGGCCCAC
TGCGGCCACCACCGGGGATCCTGCGCCCCTGCACGACCCCACGTCGGCGC
CGTGGGCCACGGCCCTGGCGCGCCGCGTGGCTGCTGAACTGCAAGCGGCG
GCTGCCGAGCTGCGAAGCCTCCCGGGTCTGCCTCCGGCCACAGCCCCGCT
GCTGGCGCGCCTGCTCGCGCTCTGCCCAGGAGGCCCCGGCGGCCTCGGCG
ATCCCCTGCGAGGCGCTGCTGCTCCTGAAGGCGCTGCAGGGCCTGCGCGTG
GAGTGGCGCGGGCGGGATCCGCGCGGGCCGGGTCGGGCACAGCGCAGCGC
GGGGGCCACCGCCGCCGACGGGCCGTGCGCGCTGCGCGAGCTCAGCGTAG
ACCTCCGCGCCGAGCGCTCCGTACTCATCCCCGAGACCTACCAGGCCAAC
AATTGCCAGGGCGTGTGCGGCTGGCCTCAGTCCGACCGCAACCCGCGCTA
CGGCAACCACGTGGTGCTGCTGCTGAAGATGCAGGCCCGTGGGGCCGCCC
TGGCGCGCCCACCCTGCTGCGTGCCCACCGCCTACGCGGGCAAGCTGCTC
ATCAGCCTGTCGGAGGAACGCATCAGCGCGCACCACGTGCCCAACATGGT
GGCCACCGAGTGTGGCTGCCGGTGACCCCTGCGCCGCGCGGACTCCTGCC
CCGAGGGTCCGGACGCGCCCCAGCTCGCGCCCCTTCCCATATTTATTCGG
ACCCCAAGCATCGCCCCAATAAAGACCAGCAAGC
```

(the sequence of the human gene);

```
AGCACCCACGATGCGGGACCTGCCTCTCACCAGCCTGGCCCTAGTGCTGT
CTGCCCTGGGGGCTCTGCTGGGGACTGAGGCCCTCAGAGCAGGAGGAGCCA
GCTGTGGGCACCAGTGGCCTCATCTTCCGAGAAGACTTGGACTGGCCTCC
AGGCATCCACAAGAGCCTCTGTGCCTGGTGGCACTGGGCGGGGACAGCA
ATGGCAGCAGCTCCCCCCTGCGGGTGGTGGGGGCTCTAAGCGCCTATGAG
CAGGCCTTCCTGGGGGCCGTGCAGAGGGCCCGCTGGGGCCCCCGAGACCT
GGCCACCTTCGGGGTCTGCAACACCGGTGACAGGCAGGCTGCCTTGCCCT
CTCTACGGCGGCTGGGGGCCTGGCTGCGGGACCCTGGGGGGCAGCGCCTG
GTGGTCCTACACCTGGAGGAAGTGACCTGGGAGCCAACACCCTCGCTGAG
GTTCCAGGAGCCCCGCCTGGAGGAGCTGGCCCCCAGAGCTGGCGCTGC
TGGTGCTGTACCCTGGGCCTGGCCCTGAGGTCACTGTGACGAGGGCTGGG
CTGCCGGGTGCCCAGAGCCTCTGCCCCTCCCGAGACACCCGCTACCTGGT
GTTAGCGGTGGACCGCCCTGCGGGGGCCTGGCGCGGCTCCGGGCTGGCCT
TGACCCTGCAGCCCCGCGGAGAGGACTCCCGGCTGAGTACCGCCCGGCTG
CAGGCACTGCTGTTCGGCGACGACCACCGCTGCTTCACACGGATGACCCC
GGCCCTGCTCCTGCTGCCGCGGTCCGAGCCCGCGCCGCTGCCTGCGCACG
GCCAGCTGGACACCGTGCCCTTCCCGCCGCCCAGGCCATCCGCGGAACTC
GAGGAGTCGCCACCCAGCGCAGACCCCTTCCTGGAGACGCTCACGCGCCT
GGTGCGGGCGCTGCGGGTCCCCCCGGCCCGGGCCTCCGCGCCGCGCCTGG
CCCTGGATCCGGACGGCCTGGCCGGCTTCGGCGGCCTAGTCAACCTG
TCGGACCCCGCGGCGCTGGAGCGCCTACTCGACGGCGAGGAGCCGCTGCT
GCTGCTGCTGAGGCCCACTGCGGCCACCACCGGGGATCCTGCGCCCCTGC
ACGACCCCACGTCGGCGCCGTGGGCCACGGCCCTGGCGCGCCGCGTGGCT
GCTGAACTGCAAGCGGCGGCTGCCGAGCTGCGAAGCCTCCCGGGTCTGCC
TCCGGCCACAGCCCCGCTGCTGGCGCCTGCTCGCGCTCTGCCCAGGAG
GCCCCGGCGGCCTCGGCGATCCCCTGCGAGCGCTGCTGCTCCTGAAGGCG
CTGCAGGGCCTGCGCGTGGAGTGGCGCGGGCGGGATCCGCGCGGGCCGGG
TCGGGCACAGCGCAGCGCGGGGGCCACCGCCGCCGACGGGCCGTGCGCGC
TGCGCGAGCTCAGCGTAGACCTCCGCGCCGAGCGCTCCGTACTCATCCCC
GAGACCTACCAGGCCAACAATTGCCAGGGCGTGTGCGGCTGGCCTCAGTC
CGACCGCAACCCGCGCTACGGCAACCACGTGGTGCTGCTGCTGAAGATGC
AGGCCCGTGGGGCCGCCCTGGCGCGCCCACCCTGCTGCGTGCCCACCGCC
TACGCGGGCAAGCTGCTCATCAGCCTGTCGGAGGAACGCATCAGCGCGCA
CCACGTGCCCAACATGGTGGCCACCGAGTGTGGCTGCCGGTGACCCCTGC
GCCGCGCGGACTCCTGCCCCGAGGGTCCGGACGCGCCCCAGCTCGCGCCC
CTTCCCATATTTATTCGGACCCCAAGCATCGCCCCAATAAAGACCAGCAA
GC
```

(the sequence of human cDNA);

```
CAAGGTCATGTCCCAGGAGGAGATAGGGACCGCCCTGCACCACAAACAGC
TCTGCTCCCTCTTATAAAGTAGGGCAGCCCAGCCCCTGGAAGCTCCCAGG
ATGCCCGGTCCATCTCTCTCTCTGGCCCTGGTGCTGTCGGCCATGGGGGC
TCTGCTGAGGCCAGGGACCCCCAGGGAAGAAGTCTTCAGCACCTCAGCCT
TGCCCAGGGAGCAGGCCACAGGCAGCGGGGCACTCATCTTTCAGCAAGCC
TGGGACTGGCCACTCTCCAGTCTCTGGCTGCCAGGCAGCCCCTCTGGACCC
CCTGTGCCTGGTGACCCTGCATGGGAGTGGCAACGGGAGCAGGGCCCCCC
TGCGGGTGGTGGGGGTCCTGAGCAGCTACGAGCAGGCCTTCCTGGAGGCT
GTGCGGCGCACCCACTGGGGCCTGAGTGACTTGACCACCTTCGCAGTGTG
CCCCGCTGGCAACGGGCAGCCTGTGCTGCCCACCTGCAGCGGCTGCAGG
CATGGCTGGGGGAGCCCGGGGGGCGGTGGCTGGTGGTCCTGCACCTGGAG
GAAGTGACGTGGGAGCCAACACCCTTGCTGAGGTTCCAGGAGCCTCCGCC
TGGAGGAGCCAGCCCCCAGAGCTGGCGCTGCTGGTGGTGTACCCAGGGC
CTGGCCTGGAGGTCACTGTCACCGGGGCTGGGCTACCTGGCACCCAGAGC
CTCTGCCTGACCGCGGACTCGGACTTCCTGGCCTTGGTCGTGGACCACCC
GGAGGGGGCCTGGCGCCGGCCTGGGTTAGCCCTTACCCTGCGGCGCCGTG
GAAATGGTGCGCTCCTGAGCACTGCCCAGCTGCAGGCGCTGCTGTTCGGT
GCGGACTCCCGCTGCTTCACACGAAAGACCCCAGCCCTGTTACTCTTGCT
GCCGGCCCGGTCTTCGGCACCGATGCCCGCGCACGGTCGGCTGGACTTGG
TGCCCTTCCCGCAGCCCAGGGCTTCCCCGGAGCCAGAGGAGGCACCGCCC
AGCGCTGATCCCTTCCTGGAGACTCTCACGCGCCTGGTGCGCGCGCTTGC
GGGACCCCCGGCCCGAGCCTCGCCACCGCGGCTGGCCTTGGACCCGGGCG
CACTGGCTGGTTTCCCGCAGGGCCAGGTCAACCTGTCGGACCCCGCGGCC
CTGGAGCGCCTGCTGGACGGCGAGGAGCCGCTGCTGCTGCTGCTGCCGCC
GACGGCAGCCACCACCGGGGTCCCCGCAACGCCGCAAGGTCCCAAGTCCC
CTCTGTGGGCCGCGGGACTAGCGCGCCGGGTGGCTGCCGAGCTTCAGGCG
GTGGCCGCCGAGCTGCGTGCCCTCCCGGGGCTGCCTCCAGCTGCCCCACC
GCTGCTGGCGCGCCTGCTGGCACTGTGCCCGGGAAACCCAGACAGCCCCG
GCGGCCCGCTGCGCGCGCTGCTGCTGCTCAAAGCGCTGCAGGGCCTGCGC
GCTGAGTGGCGCGGGCGGGAGCGGAGCGGCTCTGCACGGGCGCAGCGCAG
CGCCGGGGCCGCGGCTGCAGACGGGCCGTGCGCTCTGCGTGAGCTGAGCG
TAGACCTGCGGGCCGAGCGCTCGGTGCTCATCCCCGAGACATACCAGGCC
AACAACTGCCAGGGGGCCTGCGGCTGGCCTCAGTCGGACCGCAACCCGCG
CTACGGCAACCACGTGGTGCTGCTGCTAAAGATGCAGGCCCGCGGCGCCA
CCCTGGCGCGCCCGCCCTGCTGTGTGCCCACAGCCTACACCGGCAAGCTC
CTCATCAGCCTGTCCGAGGAGCGCATCAGTGCGCACCACGTCCCAAACAT
GGTGGCCACCGAATGCGGCTGCCGGTGACCTCGCGCCGTGCTCCTCGTGC
TGCCCCGGCCCGTATTTATTCGGACCCCGTCATTGCCCCATTAAACACGG
GAAGGC
```

(the sequence of the bovine gene): and

```
AGCTCCCAGGATGCCCGGTCCATCTCTCTCTCTGGCCCTGGTGCTGTCGG
CCATGGGGGCTCTGCTGAGGCCAGGGACCCCCAGGGAAGAAGTCTTCAGC
ACCTCAGCCTTGCCCAGGGAGCAGGCCACAGGCAGCGGGGCACTCATCTT
TCAGCAAGCCTGGGACTGGCCACTCTCCAGTCTCTGGCTGCCAGGCAGCC
CTCTGGACCCCCTGTGCCTGGTGACCCTGCATGGGAGTGGCAACGGGAGC
AGGGCCCCCCTGCGGGTGGTGGGGGTCCTGAGCAGCTACGAGCAGGCCTT
CCTGGAGGCTGTGCGGCGCACCCACTGGGGCCTGAGTGACTTGACCACCT
TCGCAGTGTGCCCCGCTGGCAACGGGCAGCCTGTGCTGCCCCACCTGCAG
CGGCTGCAGGCATGGCTGGGGGAGCCCGGGGGGCGGTGGCTGGTGGTCCT
GCACCTGGAGGAAGTGACGTGGGAGCCAACACCCTTGCTGAGGTTCCAGG
AGCCTCCGCCTGGAGGAGCCAGCCCCCAGAGCTGGCGCTGCTGGTGGTG
TACCCAGGGCCTGGCCTGGAGGTCACTGTCACCGGGGCTGGGCTACCTGG
CACCCAGAGCCTCTGCCTGACCGCGGACTCGGACTTCCTGGCCTTGGTCG
TGGACCACCCGGAGGGGGCCTGGCGCCGGCCTGGGTTAGCCCTTACCCTG
CGGCGCCGTGGAAATGGTGCGCTCCTGAGCACTGCCCAGCTGCAGGCGCT
GCTGTTCGGTGCGGACTCCCGCTGCTTCACACGAAGACCCCAGCCCTGT
TACTCTTGCTGCCGGCCCGGTCTTCGGCACCGATGCCCGCGCACGGTCGG
CTGGACTTGGTGCCCTTCCCGCAGCCCAGGGCTTCCCTGGAGCCAGAGGA
GGCACCGCCCAGCGCTGATCCCTTCCTGGAGACTCTCACGCGCCTGGTGC
GCGCGCTTGCGGGACCCCCGGCCCGAGCCTCGCCACCGCGGCTGGCCTTG
GACCCGGGCGCACTGGCTGGTTTCCCGCAGGGCCAGGTCAACCTGTCGGA
CCCCGCGCCCTGGAGCGCCTGCTGGACGGCGAGGAGCCGCTGCTGCTGC
TGCTGCCGCCGACGGCAGCCACCACCGGGGTCCCCGCAACGCCGCAAGGT
CCCAAGTCCCCTCTGTGGGCCGCGGGACTAGCGCGCCGGGTGGCTGCCGA
GCTTCAGGCGGTGGCCGCCGAGCTGCGTGCCCTCCCGGGGCTGCCTCCAG
CTGCCCCACCGCTGCTGGCGCGCCTGCTGGCACTGTGCCCGGGAAACCCA
GACAGCCCCGGCGGCCCGCTGCGCGCGCTGCTGCTGCTCAAAGCGCTGCA
GGGCCTGCGCGCTGAGTGGCGCGGGCGGGAGCGGAGCGGCTCTGCACGGG
CGCAGCGCAGCGCCGGGGCCGCGGCTGCAGACGGGCCGTGCGCTCTGCGT
GAGCTGAGCGTAGACCTGCGGGCCGAGCGCTCGGTGCTCATCCCCGAGAC
ATACCAGGCCAACAACTGCCAGGGGGCCTGCGGCTGGCCTCAGTCGGACC
GCAACCCGCGCTACGGCAACCACGTGGTGCTGCTGCTAAAGATGCAGGCC
CGCGGCGCCACCCTGGCGCGCCCGCCCTGCTGTGTGCCCACAGCCTACAC
CGGCAAGCTCCTCATCAGCCTGTCCGAGGAGCGCATCAGTGCGCACCACG
TCCCAAACATGGTGGCCACCGAATGCGGCTGCCGGTGACCTCGCGCCGTG
CTCCTCGTGCTGCCCCGGCCCGTATTTATTCGGACCCCGTCATTGCCCCA
TTAAACACGGGAAGGC
```

(the sequence of bovine cDNA); and (b) DNA sequences which hybridize to the aforementioned DNA sequences and which code on expression for a human MIS-like polypeptide or a bovine MIS-like polypeptide and preferably have a substantial degree of homology (more preferably, at least about 70% homology and most preferably at least about 80% of homology) to the aforementioned DNA sequences; and (c) DNA sequences which code on expression for a polypeptide coded for on expression by any of the foregoing DNA sequences. Recombinant DNA molecules containing these DNA sequences, hosts transformed with them and MIS-like polypeptides coded for on expression by them are also part of this invention.

The DNA sequences, recombinant DNA molecules, hosts and processes of this invention enable the production of MIS-like polypeptides for use in the treatment of ovarian cancer and other susceptible cancers.

Also within the scope of the present invention are the polypeptides selected from the group consisting of

```
MRDLPLTSLALVLSALGALLGTEALRAEEPAVGTSGLI FREDLDWPPGI P
QEPLCLVALGGDSNGSSSPLRVVGALSAYEQAFLGAVQRARWGPRDLATF
GVCNTGDRQAALPSLRRLGAWLRDPGGQRLVVLHLEEVTWEPTPSLRFQE
PPPGGAGPPELALLVLYPGPGPEVTVTRAGLPGAQSLCPSRDTRYLVLAV
DRPAGAWRGSGLALTLQPRGEDSRLSTARLQALLFGDDHRCFTRMTPALL
LLPRSEPAPLPAHGQLDTVPFPPPRPSAELEEPPSASDPFLETLTRLVRA
LRVPPARASAPRLALDPDALAGFPQGLVNLSDPAALERLLDGEEPLLLLL
RPTAATTGDPAPLHDPTSAPWATASLARRVAAELQAAAAELRSLPGLPPAT
APLLARLLALCPGGPGGLGDPLRALLLLKALQGLRVEWRGRDPRGPGRAQ
RSAGATAADGPCALRELSVDLRAERSVLIPETYQANNCQGVCGWPQSDRN
PRYGNHVVLLLKMQARGAALARPPCCVPTAYAGKLLILEERIAHHVP
NMVATECGCR
```

(the complete amino acid sequence of human MIS protein);

```
LRAEEPAVGTSGLI FREDLDWPPGI PQEPLCLVALGGDSNGSSSPLRVVG
ALSAYEQAFLGAVQRARWGPRDLATFGVCNTGDRQAALPLRRSLGAWLRD
PGGQRLVVLHLEEVTWEPTPSLRFQEPPPGGAGPPELALLVLYPGPGPEV
TVTRAGLPGAQSLCPSRDTRYLVLAVDRPAGAWRGSGLASLTLQPRGEDR
LSTARLQALLFGDDHRCFTRMTPALLLLPRSEPAPLPAHGQLDTVPFPPP
RPSAELEESPPSADPFLETLTRLVRALRVPPARASAPRLALDPDALAGFP
QGLVNLSDPAALERLLDGEEPLLLLLRPTAATTGDPAPLHDPTSAPWATA
LARRVAAELQAAAAELRSLPGLPPATAPLLARLLALCPGGPGGLGDPLRA
LLLLKALQGLRVEWRGRDPRGPGRAQRSAGATAADGPCALRELSVDLRAE
RSVLIPETYQANNCQGVCGWPQSDRNPRYGNHVVLLLKMQARGAALARPP
CCVPTAYAGKLLISLSEERISAHHVPNMVATECGCR
```

(the amino acid sequence of mature human MIS protein);

```
MP GP S L S L AL VL S AMGAL L R P GT P R E E V F S T S AL P R E Q AT GS GAL I F Q Q A
W DW P L S S L WL P GS P L DP L C L V T L HGS GNGS R AP L R V V GV L S S Y E Q AF L E A
V R R T HW GL S DL T T F AV C P AGNG Q P V L P HL Q R L Q AW L GE P GG R W L V V L HL E
E V T W E P T P L L R F Q E P P P GGAS P P E L AL L V V Y P GP GL E V T V T GAGL P GT Q S
L C L T ADS DF L AL V V DHP E GAW R R P GL AL T L R R R GNGAL L S T AQ L Q AL L F G
ADS R C F T R K T P AL L L L L P AR S S AP MP AHGR L DL V P F P Q P R AS P E P E E AP P
S ADP F L E T L T R L V R AL AGP P AR AS P P R L AL DP GAL AGF P Q GQ V NL S DP AA
L E R L L DGE E P L L L L L P P T AAT T GV P AT P Q GP K S P L W AAGL AR R V AAE L Q A
V AAE L R AL P GL P P AAP P L L AR L L AL C P GNP DS P GGP L R AL L L L K AL Q GL R
AE W R GR E R S GS AR AQ R S AGAAADGP C AL R E L S V DL R AE R S V L I P E T Y Q A
NN C Q GAC GW P Q S DR NP R Y GNHV V L L L K M Q AR GAT L AR P P C C V P T AY T GK L
L I S L S E E R I S AHHV P NMV AT E C GC R
```

(the complete amino acid sequence of bovine MIS protein);

```
R E E V F S T S AL P R E Q AT GS GAL I F Q Q AW DW P L S S L WL P GS P L DP L C L V T L H
GS GNGS R AP L R V V GV L S S Y E Q AF L E AV R R T HW GL S DL T T F AV C P AGNG Q P
V L P HL Q R L Q AW L GE P GG R W L V V L HL E E V T W E P T P L L R F Q E P P P GGAS P P E
L AL L V V Y P GP GL E V T V T GAGL P GT Q S L C L T ADS DF L AL V V DHP E GAW R R P
GL AL T L R R R GNGAL L S T AQ L Q AL L F GADS R C F T R K T P AL L L L L P AR S S AP
MP AHGR L DL V P F P Q P R AS P E P E E AP P S ADP F L E T L T R L V R AL AGP P AR AS
P P R L AL DP GAL AGF P Q GQ V NL S DP AAL L DGE E P L L L L L P P T AAT T GV
P AT P Q GP K S P L W AAGL AR R V AAE L Q AV AAE L R AL P GL P P AAP P L L AR L L A
L C P GNP DS P GGP L R AL L L L K AL Q GL R AE W R GR E R S GS AR AQ R S AGAAAD
GP C AL R E L S V DL R AE R S V L I P E T Y Q ANNC Q GAC GW P Q S DR NP R Y GNHV V L
L L K M Q AR GAT L AR P P C C V P T AY T GK L L I S L S E E R I S AHHV P NMV AT E C GC
R
```

(the amino acid sequence of mature bovine MIS protein); and MIS-like polypeptides related thereto, an anti-cancer pharmaceutical composition comprising one of the foregoing polypeptides and a pharmaceutically acceptable carrier and methods of using such compositions in treating susceptible cancers, especially cancers of the female genital tract (e.g., ovarian cancer).

BRIEF DESCRIPTION OF THE DRAWINGS

FIG. 1 depicts the amino acid sequences obtained from sequence analysis of tryptic peptides of bovine MIS. Only two of the 23 sequences obtained are shown.

FIGS. 2A-2B show the sixteen pools of chemically synthesized oligonucleotide DNA probes that were used to isolate the bovine cDNA clone.

FIGS. 3A-3H display the nucleotide sequence of the bovine gone which includes the full length cDNA sequence and the promoter region.

FIGS. 6A-6K display the nucleotide sequence of the human gene in cosmid clone chmis33. The protein sequence is indicated below the DNA sequence. It is interrupted in four places by introns.

FIG. 7 depicts the construction of plasmids pBG311.hmis and pBG312.hmis that may be used to express the human DNA sequence of the invention.

Figure 4:
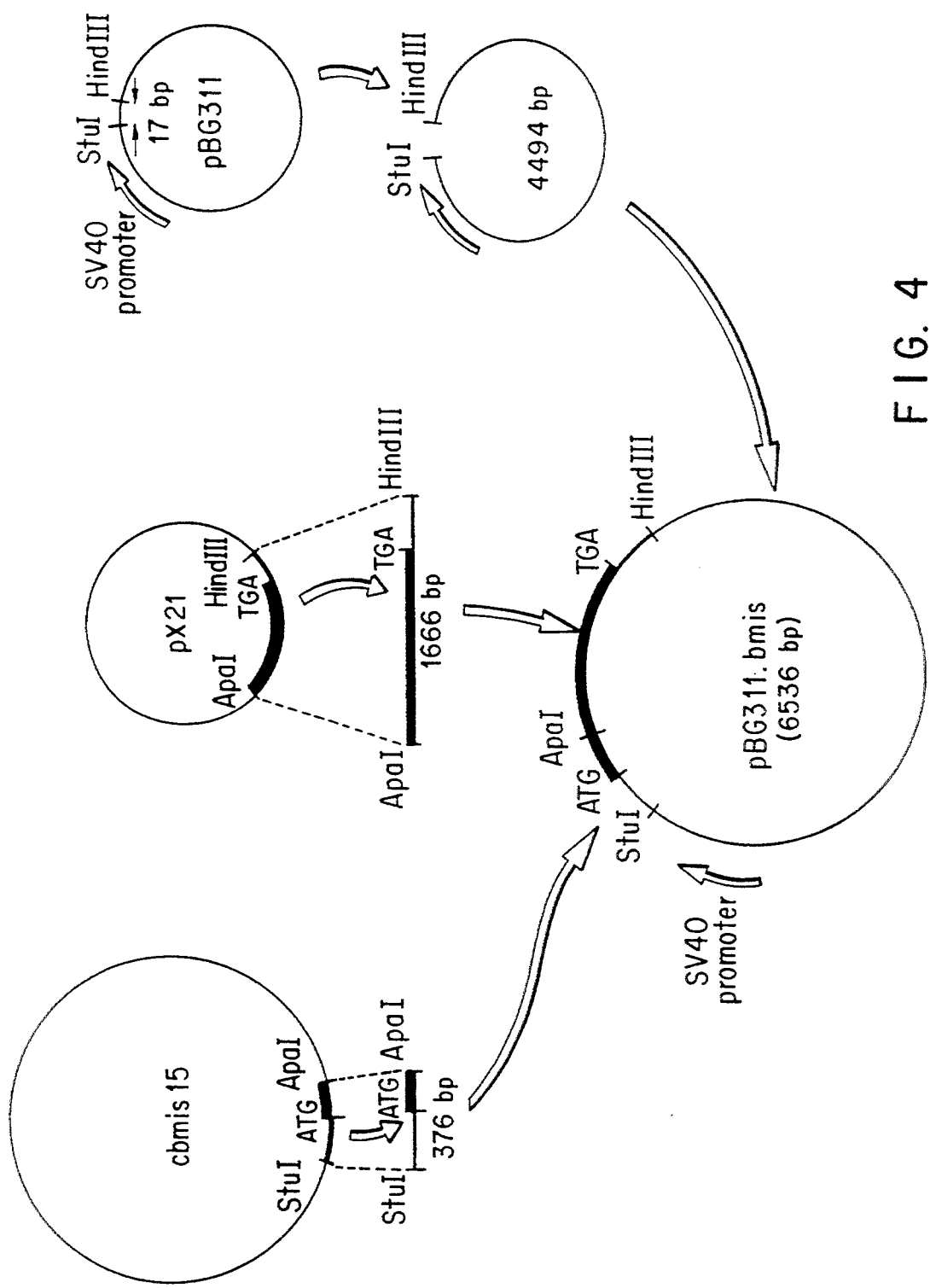
FIG. 4 depicts the construction of plasmid pBG311.bmis which may be used to express the bovine DNA sequence of the invention.

In order that the invention herein described may be more fully understood, the following detailed description is set forth.

In the description, the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

<u>GCT</u> <u>GGT</u> <u>TGT</u> AAG—Ala—Gly—Cys—Lys

G <u>CTG</u> <u>GTT</u> <u>GTA</u> AG—Leu—Val—Val

GC <u>TGG</u> <u>TTG</u> <u>TAA</u> G—Trp—Leu—(STOP)

Polypeptide—A linear array of amino acids connected one to the other by peptide bonds between the α-amino, and carboxy groups of adjacent amino acids.

Genome—The entire DNA of a cell or a virus. It includes, inter alia, the structural gene coding for the polypeptides of the substance, as well, as operator, promoter and ribosome binding and interaction sequences, including sequences such as the Shine-Dalgarno sequences.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

cDNA clone—A clone containing a DNA insert that was synthesized from mRNA and does not contain introns. The vector can be a plasmid or a phage.

Genomic clone—A clone containing a DNA insert which is a fragment of a genome (i.e., isolated from total cellular DNA). It can contain introns which interrupt the protein coding region of the gene. The vector can be a plasmid, a phage or a cosmid.

Exon—Portions of the gene which after transcription are maintained in the mRNA following splicing of the precursor RNA.

Intron—Portions of the gene which are spliced out after transcription.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($TET^R$) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cosmid—A plasmid containing the cohesive end ("cos") site of bacteriophage λ. Cosmids may, because of the presence of the cos site, be packaged into λ coat protein and used to infect an appropriate host. Because of their capacity for large fragments of foreign DNA, cosmids are useful as cloning vehicles.

Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

Expression Control Sequence—A sequence of nucleotides that controls and regulates expression of genes when operatively linked to those genes. They include the lac system, the β-lactamase system, the trp system, the tac and trc systems, the major operator and promoter regions of phage λ, the control region of fd coat protein, the early and late promoters of SV40, promoters derived from polyoma virus and adenovirus, metallothionine promoter's, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells and their viruses or combinations thereof. For mammalian cells the gene can be linked to a eukaryotic promoter such as that for the SV40 early region coupled to the gene encoding dihydrofolate reductase and selectively amplified in Chinese hamster ovary cells to produce a cell line containing many copies of actively transcribed eukaryotic genes.

MIS-Like Polypeptide—A polypeptide displaying a biological or immunological activity of an MIS protein. As used herein, the phrase "biological activity of an MIS protein" shall be understood to mean that the MIS-like polypeptide has a cross section of biological activity which is substantially similar to that of a natural MIS protein (e.g., it is able to stimulate regression of the Mullerian ducts or is cytotoxic to one or more types of ovarian tumor cells, for example, the cell line HOC-21, and preferably, it both stimulates regression of the Mullerian ducts and is cytotoxic to one or more types of ovarian tumor cells). As used herein, the phrase "immunological activity of an MIS protein" shall be understood to mean the ability of an MIS-like polypeptide to cross-react with an antibody which is specific for a natural MIS protein. An example of such an antibody is disclosed in U.S. Pat. No. 4,487,833. An MIS-like polypeptide may include amino acids in addition to those of a native MIS protein or it may not include all of the amino acids of native MIS protein. For example, it may include an N-terminal methionine. Also, this polypeptide may be a mature protein or an immature protein or a protein derived from an immature protein (for example, a protein wherein only a portion of the signal sequence has been cleaved). Examples of such polypeptides are derivatives of MIS polypeptides which have been prepared by modification of the MIS amino acid sequence to achieve an improvement in properties, e.g., greater storage stability or increased half-life in vivo. As used herein, the phrase "MIS-like polypeptides derived therefrom" shall be understood to mean not only a claimed MIS-polypeptide (e.g., bovine MIS or human MIS) but also various related polypeptides of the types described in this paragraph.

The present invention relates to DNA sequences and recombinant DNA molecules coding for MIS polypeptides and processes for the production of those polypeptides.

In our isolation and cloning of a DNA sequence of this invention, we adopted a selection strategy based upon bovine MIS protein. Accordingly, we purified a bovine MIS protein from bovine testes and determined the amino acid sequence of various fragments of that protein. Based on those protein sequences, we then synthesized several antisense oligonucleotide DNA probes corresponding to those regions of purified bovine protein which had minimal nucleotide degeneracy. We then used these probes to screen a bovine cDNA library comprising *E. coli* cells containing bovine testis cDNA sequences inserted into a phage cloning vector.

For screening, we hybridized the oligonucleotide probes to the bovine cDNA library utilizing a plaque hybridization screening assay and we selected clones hybridizing to a number of our probes. After isolating and subcloning the selected bovine cDNA inserts into plasmids, we determined their nucleotide sequences and compared them to our amino acid sequences from peptides of purified bovine MIS protein. As a result of this comparison, we found that the nucleotide sequences of all clones isolated coded for amino acid sequences of bovine MIS protein.

We used the insert of one bovine MIS cDNA clone (pS21) to isolate the human MIS gene from a human cosmid library and a partial cDNA clone from a human cDNA library. We made the human cDNA library from total RNA extracted from newborn human testis.

The cDNA sequences or genomic DNA sequences of this invention can be operatively-linked to expression control sequences and used in various mammalian or other eukaryotic or prokaryotic host cells to produce the MIS-like polypeptides coded for by them. In addition, the cDNA-sequences or genomic DNA sequences of the invention are useful as probes to screen human cDNA libraries for other sequences coding for MIS-like polypeptides.

The human genomic DNA sequence, described above, has several introns. DNA sequences and recombinant DNA molecules wherein one or more or all of these introns are deleted are also considered to be within the scope of the present invention.

The bovine and human MIS-like polypeptides (and preferably the human MIS-like polypeptides) of this invention are useful as anti cancer drugs. For example, such compositions may comprise an anti-cancer effective amount of MIS-like polypeptide of this invention and a pharmaceutically acceptable carrier. Such therapies generally comprise a method of treating patients in a pharmaceutically acceptable manner with those compositions.

Generally, the pharmaceutical compositions of the present invention may be formulated and administered using methods similar to those used for other pharmaceutically important polypeptides (e.g., alpha-interferon). Thus, the polypeptides may be stored in lyophilized form, reconstituted with sterile water just prior to administration, and administered intravenously. Preferably, the pharmaceutical formulations of the present invention will be administered in dosages and modes of administration similar to those that have been used for MIS protein as disclosed in U.S. Pat. No. 4,510,131, the disclosure of which is hereby incorporated herein by reference.

A wide variety of host/cloning vehicle combinations may be employed in cloning or expressing the MIS-like polypeptide DNA sequences prepared in accordance with this invention. For example, useful cloning or expression vehicles may consist of segments of chromosomal, non-chromosomal and synthetic DNA sequences, such as various known derivatives of SV40 and known bacterial plasmids, e.g., plasmids from *E. coli* including col E1, pCR1, pBR322, pMB9 and their derivatives, wider host range plasmids, e.g., RP4, phage DNAs, e.g., the numerous derivatives of phage λ, e.g., NM 989, and other DNA phages,.e.g., M13 and filamentous single-stranded DNA phages and vectors derived from combinations of plasmids and phage DNAs such as plasmids which have been modified to employ phage DNA or other expression control sequences or yeast plasmids such as the 2μ plasmid or derivatives thereof. For cDNA cloning, the preferred expression vector is λgt10 and the preferred host is *E. coli* BNN102. For animal cell expression, the preferred expression vectors are pBG311 and pBG312 in Chinese hamster ovary (CHO) cells.

Within each specific cloning or expression vehicle, various sites may be selected for insertion of the MIS-like polypeptide DNA sequences of this invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

Various expression control sequences may also be chosen to effect the expression of the DNA sequences of this invention. These expression control sequences include, for example, the lac system, the β-lactamase system, the trp system, the tac system, the trc system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, promoters for mammalian cells such as the SV40 early promoter, adenovirus late promoter and metallothionine promoter, and other sequences known to control the expression of genes of prokaryotic or eukaryotic cells or their viruses and various combinations thereof. In mammalian cells, it is additionally possible to amplify the expression units by linking the gene to that for dihydrofolate reductase and applying a selection to host Chinese hamster ovary cells.

For expression of the DNA sequences of this invention, these DNA sequences are operatively-linked to one or more of the above-described expression control sequences in the expression vector. Such operative linking, which may be effected before or after the chosen MIS-like polypeptide DNA sequence is inserted into a cloning vehicle, enables the expression control sequences to control and promote the expression of the DNA sequence.

The vector or expression vehicle, and in particular the sites chosen therein for insertion of the selected DNA fragment and the expression control sequence employed in this invention, is determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a particular MIS-like polypeptide sequence is determined by a balance of these factors, not all selections being equally effective for a given case.

It should also be understood that the DNA sequences coding for the MIS-like polypeptides of this invention that are inserted at the selected site of a cloning or expression vehicle may include nucleotides which are not part of the actual gene coding for the MIS-like polypeptide or may include only a fragment of the entire gene for that polypeptide. It is only required that whatever DNA sequence is employed, a transformed host will produce a MIS-like polypeptide. For example, the MIS-like polypeptide-related DNA sequences of this invention may be fused in the same reading frame in an expression vector of this invention to at least a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired MIS-like polypeptide-related DNA sequence, improve purification or permit secretion, and preferably maturation, of the MIS-like polypeptide from the host cell. The MIS-like polypeptide-related DNA sequence may alternatively include an ATG start codon, alone or together with other codons, fused directly to the sequence encoding the first amino acid of a mature native MIS-like polypeptide. Such constructions enable the production of, for example, a methionyl or other peptidyl-MIS like polypeptide, that is part of this invention. This N-terminal methionine or peptide may either then be cleaved intra- or extra-cellularly by a variety of known processes or the MIS-like polypeptide with the methionine or peptide attached may be used, uncleaved, in the pharmaceutical compositions and methods of this invention.

The cloning vehicle or expression vector containing the MIS-like polypeptide coding sequences of this invention is employed in accordance with this invention to transform an appropriate host so as to permit that host to express the MIS-like polypeptides for Which the DNA sequence codes.

Useful cloning or expression hosts may include strains of E. coli, such as E. coli C600, E. coli ED8767, E. coli DH1, E. coli LE392, E. coli HB 101, E. coli X1776, E. coli X2282, E. coli MRCI, E. coli BNN102, E. coli JM83, E. coli JA221, and strains of Pseudomonas, Bacillus, and Streptomyces, yeasts and other fungi, animal hosts, such as CHO cells, COS cells or mouse cells, other animal (including human) hosts, plant cells in culture or other hosts.

The selection of an appropriate host is also controlled by a number of factors recognized by the art. These include, for example, compatibility with the chosen vector, toxicity of proteins encoded by the hybrid plasmid, susceptibility of the desired protein to proteolytic degradation by host cell enzymes, contamination or binding of the protein to be expressed by host cell proteins difficult to remove during purification, ease of recovery of the desired protein, expression characteristics, bio-safety and cost. A balance of these factors must be struck with the understanding that not all host vector combinations may be equally effective for either the cloning or expression of a particular recombinant DNA molecule.

It should be understood that the MIS-like polypeptides (prepared in accordance with this invention in those hosts) may include polypeptides in the form of fused proteins (e.g., linked to a prokaryotic, eukaryotic or combination N-terminal segment to direct excretion, improve stability, improve purification or improve possible cleavage of the N-terminal segment), in the form of a precursor of MIS-like polypeptides (e.g., starting with all or parts of a MIS-like polypeptide signal sequence or other eukaryotic or prokaryotic signal sequences), in the form of a mature MIS-like polypeptide, or in the form of an fmet-MIS-like polypeptide. As pointed out above, the phrase "MIS-like polypeptides derived, therefrom", as used herein, shall be understood to include such MIS-like polypeptides.

One particularly useful form of a polypeptide in accordance with this invention, or at least a precursor thereof, is a mature MIS-like polypeptide with an easily cleaved amino acid or series of amino acids attached to the amino terminus. Such construction allows synthesis of the polypeptide in an appropriate host, where a start signal that may not be present in the mature polypeptide is needed, and then cleavage in vivo or in vitro of the extra amino acids to produce mature MIS-like polypeptides. Such methods exist in the art. See, e.g., U.S. Pat. Nos. 4,332,892, 4,338,397, and 4,425,437. The polypeptides may also be glycosylated, like native MIS protein, unglycosylated, or have a glycosylation pattern different than that of native MIS protein. Such glycosylation will result from the choice of host cell or post-expression treatment chosen for the particular MIS-like polypeptide.

The polypeptides of the invention also include MIS-like polypeptides that are coded on expression by DNA sequences characterized by different codons for some or all of the codons of the present DNA sequences. These substituted codons may code for amino acids identical to those coded for by the codons replaced but result in higher yield of the polypeptide. Alternatively, the replacement of one or a combination of codons leading to amino acid replacement or to a longer or shorter MIS-like polypeptide may alter its properties in a useful way (e.g., increase the stability, increase the solubility or increase the therapeutic activity).

In order that this invention may be better understood, the following examples are set forth. These examples are for purposes of illustration only and are not to be construed as limiting the scope of the invention in any manner.

EXAMPLES

EXAMPLE 1

SEQUENCING OF BOVINE MIS PROTEIN

We isolated bovine MIS protein from newborn bovine testis by the procedure of Budzik et al. (Cell, 34, 307–314 (1983)). After eluting it from the Matrix Gel. Green A column with 0.5M NaCl, we concentrated the bovine MIS fraction (Green-3) and dialyzed against PBS and 0.01% Nonidet-P40 and stored at −70°.

Analytical reducing SDS-PAGE indicated that MIS (Green-3 fraction) contained two predominant polypeptides of 74 Kd and 70 Kd, and several minor components including species near 140 and 95 Kd. We obtained highly purified samples of the 74 and 70 Kd species by combination of semi-prep SDS-PAGE followed by electroelution. Each of these was subjected to N-terminal analysis. Both the 70 Kd and the 74 Kd polypeptides had the same N-terminus (ArgGluGluVal-PheSer).

We separately digested approximately 1 nanomole each of the reduced and carboxymethylated 74 Kd and 70 Kd MIS polypeptides with TPCK-trypsin. After carboxymethylation, we resuspended purified polypeptides in O.1M $NH_4HCO_3$ plus 0.1 mM $CaCl_2$, and then incubated with TPCK trypsin for 16 h at 37° C. During this incubation, we added trypsin three times to a final concentration of 2.0% of total protein at time zero, 4.0% after 4 h and 6.0% after 12 h.

We resolved the cleavage fragments from these digestions by high pressure liquid chromatography utilizing a gradient of acetonitrile from 0–75% in 0.1% trifluoroacetic acid to elute peptides bound to a C18 column.

The two tryptic maps were very similar, indicative of the same primary structure and suggesting that the 70 Kd polypeptide derives from the 74 Kd polypeptide. Therefore, we combined selected conserved peaks from each digest and subjected them to sequence analysis using a gas phase sequencer (Applied Biosystems 470A). We analyzed PTH-amino acids by high pressure liquid chromatography on a 5 µm cyano column (Hypersil), using a gradient of acetonitrile:methanol (4:1) from 15–55% in 0.02M sodium acetate (pH 5.7).

Tryptic digestion produced over 20 peaks. Six of these yielded protein sequence. The sequence of one tryptic peptide, #T105–106, is shown in FIG. 1.

Analytical digests of $^{125}$I-labelled 74 Kd and 70 Kd MIS by trypsin or *S. aureus* V8 protease showed that most of the peptides generated were larger than 10 Kd and were recovered in low yield by HPLC on a C18 column. Using both SDg-urea PAGE and HPLC analysis, we again observed that conserved cleavage products occurred between 70 Kd and 74 Kd MIS, confirming that the two polypeptides are related.

In order to increase the extent of digestion by TPCK-trypsin at basic pH, we succinylated 1 nmole of MIS prior to digestion, and separated the resultant peptides on a C8 column (90% yield). We obtained six more peptide sequences, ranging from 5 to 16 residues; two of these confirmed previously obtained sequences. The sequence of tryptic peptide #T81 is shown in FIG. 1.

We further improved the efficiency of digestion of MIS by TPCK-trypsin by including 2M urea in the digestion. Using peptides produced in this manner, we obtained eleven additional peptide sequences. In total, we obtained 23 peptide sequences, two of which are shown in FIG. 1.

EXAMPLE 2

SYNTHESIS OF OLIGONUCLEOTIDE DNA PROBES

After the amino acid sequences of various regions of the bovine MIS protein were determined (see FIG. 1), we chemically synthesized two pools of antisense oligonucleotide DNA probes that coded for some of those protein sequences (see FIGS. 2A–2B). We synthesized the two pools (1–4 and 9–12) shown in FIGS. 2A–2B because they corresponded to regions of the MIS protein that have minimal nucleic acid degeneracy. For each amino acid sequence, we synthesized mixtures of probes complementary to all possible codons. The probes were complementary to the DNA sequences which code for the amino acid sequence, i.e., the probes were antisense,, to enable the probes to recognize the corresponding sequences in mRNA as well as in DNA. The amino acid sequences of the two selected regions of the MIS protein and all the possible nucleotide codon combinations that encode them are shown in FIG. 2A–2B. Coding degeneracies are indicated as follows: N=C, T, A, or G; R=A or G; Y=C or T; and H=A, C, or T.

The two pools of the probes, derived from sequences in the tryptic fragments T105–106 and T81 of FIG. 1, were 17-mers with 256 fold degeneracy or 20-mers with 512 fold degeneracy respectively. We synthesized each pool in groups of four, by splitting at a degenerate codon in the middle of the probe. Thus, we prepared the 256 fold degenerate 17-met of T105–106 in four subpools [1–4] of 64 and the 512 fold degenerate 20-mer of T81 in four pools [9–12] of 128. This allowed us to reduce the degeneracy by using them individually on Northern blots in order to distinguish the subpool that contained the correct sequence (see below). We synthesized probes on an Applied Biosystems 380A DNA synthesizer and purified them by gel electrophoresis. We labelled the probes by using [γ-32P]-ATP and polynucleotide kinase (Maxam and Gilbert, *Proc. Natl. Acad. Sci.*, 74, 560 (1977)).

We used Northern analysis to reduce the degeneracy of the two probe regions 1–4 and 9–12. We hybridized the probes individually to Northern blots with RNA from two-week old and three-month old bovine testis, and adult bovine kidney. Since only two-week old bovine testis contains biologically active MIS, we expected that the Northern analysis would distinguish which probe within a group contained the correct MIS sequence. The less degenerate probe would then be used to screen the cDNA library. Northern blots with MIS probes 1–4 suggested that probe 2 contained the correct oligomer sequence, while Northern blots with MIS probes 9–12 indicated that probe 12 contained the correct oligomer sequence. In both cases, a 2000 nucleotide transcript was observed in the RNA from 2 week old bovine testis, and not in the other RNAs. We broke subpool 2 into four subpools (13–16) of 16-fold degeneracy, while probe 12was broken into four subpools (17–20) of 32-fold degeneracy. Northern analysis with these probes confirmed that the correct choices were made, since one subpool from probe region 1–4 (16) and one subpool from probe region 9–12 (18) both hybridized to a 2000 nucleotide transcript in the two-week old bovine testis RNA. The transcript was not present in 3-month old bovine testis or kidney.

EXAMPLE 3

CONSTRUCTION AND SCREENING OF A BOVINE TESTIS cDNA LIBRARY

We constructed a bovine cDNA library from poly A+ mRNA isolated from bovine testis. We inserted the cDNA sequences into λgt10 and amplified the sequences in *E. coli* BNN 102 cells.

A. Extraction of RNA from Bovine Testis

We obtained testis from two week old calves immediately, after slaughter. We removed the semi-niferous tubules from the tunica albuginea and quickly froze them in Liquid nitrogen. We pulverized about 10 g of the frozen tissue and homogenized the resulting material in 100 ml of extraction buffer (4M guanidine thiocyanate, 0.5% SDS, 25 mM sodium citrate, 0.1% Sigma anti-foam) using a polytron for 2 min at high speed. We centrifuged the homogenate for 20 min at 8,000 rpm in a Sorvall RC2B centrifuge at 4° C. We recovered 75 ml of the supernatant and layered it on 30 ml (3 tubes containing 10 ml each) of a CsCl cushion (5.7M CsCl, 25 mM NaOAc pH 5.0, 1 mM EDTA) and then centrifuged it in a SW28 rotor at 22,000 rpm for 16 hrs. We resuspended the pellets in 10 ml of 10 mM Tris-HCl (pH 7.4), 1 mM EDTA, and 0.1% SDS. We then ethanol-precipitated the nucleic acids in 0.3M sodium acetate at −20° C. overnight and pelleted them at 14 K rpm in a Sorvall RC2B centrifuge (SS34 rotor) at 4° C. for 20 min. We resuspended the pellets in 5 ml 0.3M sodium acetate, and again ethanol-precipitated the nucleic acids as described above. We resuspended the final pellet in 300 µl H$_2$O and stored it at −20° C. We enriched this RNA preparation for poly(A) RNA by passage over an oligo(dT)-cellulose column (PL Biochem).

B. Construction Of A cDNA Library From Two Week Old Bovine Testis Poly A+ mRNA In λGT10

1. cDNA Synthesis

We synthesized cDNA from 25 μg poly A+ mRNA isolated from 2 week old bovine testis as described above. We diluted the mRNA to 500 μg/ml in H$_2$O and denatured by treatment with methyl-mercury hydroxide (CH$_3$H$_g$OH). We then added 1M CH$_3$H$_g$OH (Alfa Venetron) to 50 mM. 5 μl of 50 mM CH$_3$H$_g$OH was added to 25 μg of mRNA in 50 μl H$_2$O and incubated for 10 min. at room temperature. We terminated the reaction by adding 10 μl of 1.4M β-mercaptoethanol.

We then added the denatured mRNA mixture to a reaction mixture consisting of 0.1M Tris-HCl (pH 813) at 42°C., 0.01M MgCl$_2$, 0.01M DTT, 1mM dATP, 0.5 mM dCTP and 50μCi$^3$H-dCTP (25.7 Ci/mmol, New England Nuclear), 1 mM dGTP, 1 mM dTTP, 2.5 mM Vanadyl Ribonucleoside complex (Bethesda Research Labs), 20 μg oligo dT 12–18 (PL Biochem), and 196 U AMV Reverse Transcriptase (Seikagaku America). The final volume of the reaction mixture was 200 μl. We incubated the mixture for 3 minutes at room temperature and 3 hours at 44° C. and then terminated the reaction by adding 1/20 vol. 0.5M Na$_2$EDTA (pH 8.0).

We then extracted the reaction mixture with a mixture of TE saturated phenol and chloroform (50:50). (TE buffer is 10 mM Tri s-HCl, pH 7.0, 1 mM Na$_2$-EDTA.) We then re-extracted the organic phase with TE buffer and we chromatographed the combined aqueous phases through a 5 ml sterile pipet containing a 7×29 cm bed of Sephadex G150 in 0.01M Tris-HCl (pH 7.4), 0.1M NaCl, 0.01M Na$_2$EDTA, 0.05% SDS. We counted an aliquot of each fraction in an LKB liquid scintillation counter. We pooled the front peak minus tail and we precipitated the cDNA with 2.5 vol. 95% ethanol at −20° C. The yield of cDNA was 8.1 μg obtained as a cDNA-mRNA hybrid.

2. Double Strand Synthesis

We resuspended the cDNA in H$_2$O and we set up duplicate second strand reactions each containing 4 μg cDNA. Each 400 μl reaction contained 0.02M Tris-HCl pH 7.5, 0.1M KCl, 0.005M MgCl$_2$, 0.5 mM dATP+100 μCi α-dATP$^{32}$ (3000 Ci/mmol, New England Nuclear), 1 mM dCTP, 1 mM dGTP, 1 mM dTTP, 100 u DNA Pol 1 Klenow Fraction (Boehringer Mannheim), and 4 U RNase H (P.L. Biochem). We incubated the reactions for 1 hour at 12° C., 1.5 hour at room temperature and then terminated the reactions by addition of 1/20 vol. 0.5M Na$_2$EDTA pH 8.0. We then extracted the reaction mixtures with phenol:chloroform as in the cDNA synthesis step described in the preceding paragraph and precipitated the extracted material by addition of 0.2 vol. 10M ammonium acetate and 2.5 vol. 95% ethanol at −70° C. for 20 min. We warmed the resulting mixtures to room temperature, and then spun for 15 min. in an Eppendorf centrifuge to pellet the double stranded cDNA. We resuspended the pellets in TE Buffer and repeated the precipitation with ammonium acetate (2M final concentration) and ethanol two times.

We dried the pellets in a speed vac and then resuspended them in 100 μl TE buffer. We then added 25 μg boiled RNase A (Sigma), incubated the mixture at 37° C. for 30 min., extracted with phenol:chloroform and chromatographed through Sephadex G150 as described above for the cDNA synthesis step.

To assure blunt ends, we resuspended the double stranded cDNA in H$_2$O and added it to a reaction mixture containing 0.033M Tris acetate pH 7.8, 0.066M potassium acetate, 0.01M Mg acetate, 0.17 mM DTT, 88 μg BSA, 0.25 mM dATP, dCTP, dGTP, dTTP, and 18 U T$_4$ DNA polymerase (New England Biolabs). The final volume of the reaction was 300 μl. We incubated the reaction for 1 hour at 37° C., and then extracted and precipitated with 2M ammonium acetate and 2.5 vol. 95% ethanol two times as described above for the second strand synthesis step.

We then ligated 2 μg of the blunt ended cDNA to a unique oligomer linker, formed by annealing linker 27, a 22-met with the sequence 5' AATTGAGCT CGA GCG CGG CCG C to 5' phosphorylated linker 28, an 18-mer with the sequence 5' GCG GCC GCG CTC GAG CTC 3'. The annealed linker contained a phosphorylated blunt end for ligation to blunt end cDNA and a non-phosphorylated 5' protruding sequence (AATT) for ligation to EcoR1 digested λgt10. The linker contained recognition sequences for the following restriction enzymes: Alu1, Ava1, Ban2, Bsp12, Fnu4H, FnuD2, Hal3, Hgi Al, Hhal, HinP1, Not1, Sst1, Xho1, Xma3.

We ligated 2μg of linker 27-28 to 2 μg cDNA in 0.05M Tris-HCl pH 7.8, 0.01M MgCl$_2$, 0.03M NaCl, 1 mM Spermidine, 0.2 mM Na$_2$EDTA, 2 mM DTT, 100 μg/ml BSA, 0.4 mM ATP, and 1000 U T$_4$ DNA ligase (New England Biolabs) in 26 μl final vol. at 4° C. for 24 hours. In order to remove excess linker and to size fractionate the cDNA, we extracted the ligation reaction with a mixture of TE saturated phenol and chloroform. We re-extracted the organic layer with TEN Buffer (0.01M Tris-HCl pH 7.5, 0.1M NaCl, and 1 mM Na$_2$EDTA) and the combined aqueous layers were chromatographed on a 1×30 cm Biogel A50 (BioRad) column which had been previously equilibrated in TEN buffer. We ran aliquots of the column fractions on a 1% agarose gel in TBE buffer (0.089M Tris-HCl, 0.089M boric acid and 2.5 mM Na$_2$EDTA) and we dried the gel and exposed it to Kodak XAR-5 film at −70° C. We pooled fractions containing cDNA larger than 500 bp and ethanol precipitated them. The yield of size fractionated double stranded cDNA was 900 ng.

3. Library Construction

We mixed 6μg of EcoR1 cut λGT1O with ng cDNA in 0.05M Tris-HCl pH 7.8, 0.01M MgCl$_2$, 0.03M NaCl, 1 mM Spermidine, 0.2 mM Na$_2$EDTA, 2 mM DTT, and 100 μg/ml BSA in 31.2 μl. We heated these components. to 70° C. for 3 min., 45° C. for 15 min., cooled on ice, and then spun them for 5 sec in an Eppendorf centrifuge. We adjusted the reaction mixture to 0.25 mM ATP and 2000 U T$_4$ DNA ligase (NEB) and then incubated for 16 hours at 15° C. We packaged 3.4 aliquots of the ligation into phage particles using Amersham packaging mix, according to the protocol supplied by Amersham, and used the packaged DNA to infect E. coli BNN102 cells. Plating of the library yielded 5.4×10$^6$ independent plaques which we amplified and CsCl banded. 41% of the plaques had inserts which indicated a library complexity of 2.2×10$^6$ recombinants. The titer of the CsCl banded phage was 1.6×10$^{13}$ PFU/ml.

C. Screening Of The Library

We screened the library with the labeled oligonucleotide probe 16 for nucleotide sequences that encoded MIS protein sequences using the plaque hybridization screening technique of Benton and Davis (Science, 196, 180 (1977)).

We pelleted an overnight culture of BNN102 cells in L broth and 0.2% maltose and resuspended it in an equal volume of SM buffer (50 mM Tris-HCl, pH 7.5 100 mM NaCl 10 mM MgSO$_4$, and 0.01% gelatin)

Thereafter, we pre-adsorbed 0.3 ml of cells with $5 \times 10^4$ phage particles at room temperature for 15 min. We then diluted the suspension to 8 ml in LB plus 10 mM MgSO$_4$ and 0.7% agarose at 55° C. and plated it on LB Mg plates. We made thirty such plates and then incubated the plates at 37° C. for approximately 8 hours until plaques were nearly touching. We then chilled the plates at 4° C. for 1 hour to allow the agarose to harden.

We then placed nitrocellulose filters onto the plates containing the recombinant plaques for 5 min., and then lifted and lysed the filters by placing them onto a pool of 0.5N NaOH/1.5M NaCl for 5 min, and then submerged them for 5 min. in the same buffer. We then neutralized the filters by submerging in 0.5M Tris-HCl (pH 7.4), 1.5M NaCl, two times for 5 min each., We rinsed them for 2 min. in 1M NH$_4$OAc, air dried them, and baked them for 2 hours at 80° C.

We prehybridized and hybridized the filters to oligonucleotide probe 16 in 0.2% polyvinyl-pyrrolidone, 9.2% ficoll (MW 400,000), 0.2% bovine serum albumin, 0.05M Tris-HCl (pH 7.5), 1M sodium chloride, 0.1% sodium pyrophosphate, 1% SDS, 10% dextran sulfate (MW 500,000) and 100 μg/ml tRNA. We detected hybridizing λ-cDNA sequences by autoradiography.

By means of this technique, we picked and rescreened 19 positive plaques at lower density using the same probe.

We isolated the DNA of these clones, digested it with XhoI, and hybridized it with oligomer probes 16 and 18 using the Southern blot technique (E. M. Southern, *J. Mol. Biol.*, 98, pp. 503–18 (1975)). Nine of the clones contained inserted cDNA which hybridized not only to probe 16 that encodes tryptic peptide T105-106, but also to probe 18 that encodes tryptic peptide T81.

We digested the DNA of clone λ8.21 with SacI, isolated the 2000 bp insert, and subcloned the fragment into pUC18 to produce recombinant plasmid pS21. We also removed the insert of clone λ8.21, using XhoI, and subcloned it unto pUC18 to produce recombinant plasmid pX21. We then sequenced this plasmid by the method of Maxam and Gilbert (*Proc. Natl. Acad. Sci.*, 74, 560 (1977)). This analysis demonstrated that the clone pS21 contained nucleotide sequences which corresponded to the amino acid sequences of the bovine MIS protein. Within the 2000 bp of this insert, were DNA sequences that encoded all 23 peptides that had been sequenced including the mature N-terminus (i.e., Arg Glu Glu Val Phe Set). The clone contained 30 bp of sequence upstream encoding 10 amino acids of what was presumably a leader sequence.

In order to confirm that the DNA sequence for the entire mature protein had been obtained, we isolated the genomic clone for bovine MIS (cbmis15) from a cosmid library and sequenced the 5' end by the method of Church and Gilbert (*Proc. Natl. Acad. Sci.*, 81, 1991–95 (1984)). This provided sequence upstream from the 5' end of the insert in clone pS21. An ATG was located in the same reading frame as the mature protein sequence, 72 bp upstream of the Arg residue at the mature N-terminus. This 72 bp encodes a 24 amino acid leader. The first 16 or 17 amino acids of this leader appear to constitute a signal sequence, which enables the protein to be secreted (deduced from Von Heijne analysis, *Eur. J. Biochem.*, 133, 17–21 (1983)). The remaining 7 or 8 amino acids are subsequently cleaved off to generate the mature protein. (It is not clear whether this cleavage is necessary to activate the protein.) A promoter sequence TATA is located upstream from the initiating methionine (34bp) suggesting that the 5' untranslated region is very short. We confirmed this by the following primer extension experiment which showed that RNA initiation occurs about 10 nucleotides upstream of the initiating ATG. An anti-sense kinased oligomer (5'-A*GTCCCAGGCTTGCTGAAAGAT-GAGTGCCC 3') was hybridized to poly A+ RNA from bovine testes and extended with reverse transcriptase. The primer extension product was sized on a sequencing gel at 166–167 nucleotides. This placed the 5' end of the mRNA 10 or 11 nucleotides upstream from the initiating ATG. This analysis proved that we had isolated the entire gene for bovine MIS which encodes for a 58 Kd protein. The DNA sequence is shown in FIG. 3A–3H. The first 100 bp contain the promoter and 5' untranslated region. This is followed by 1875 bp that encode the bovine MIS protein and 81 bp of 3' untranslated Sequence.

EXAMPLE 4

ISOLATION OF THE HUMAN GENOMIC CLONE

Figure 5:
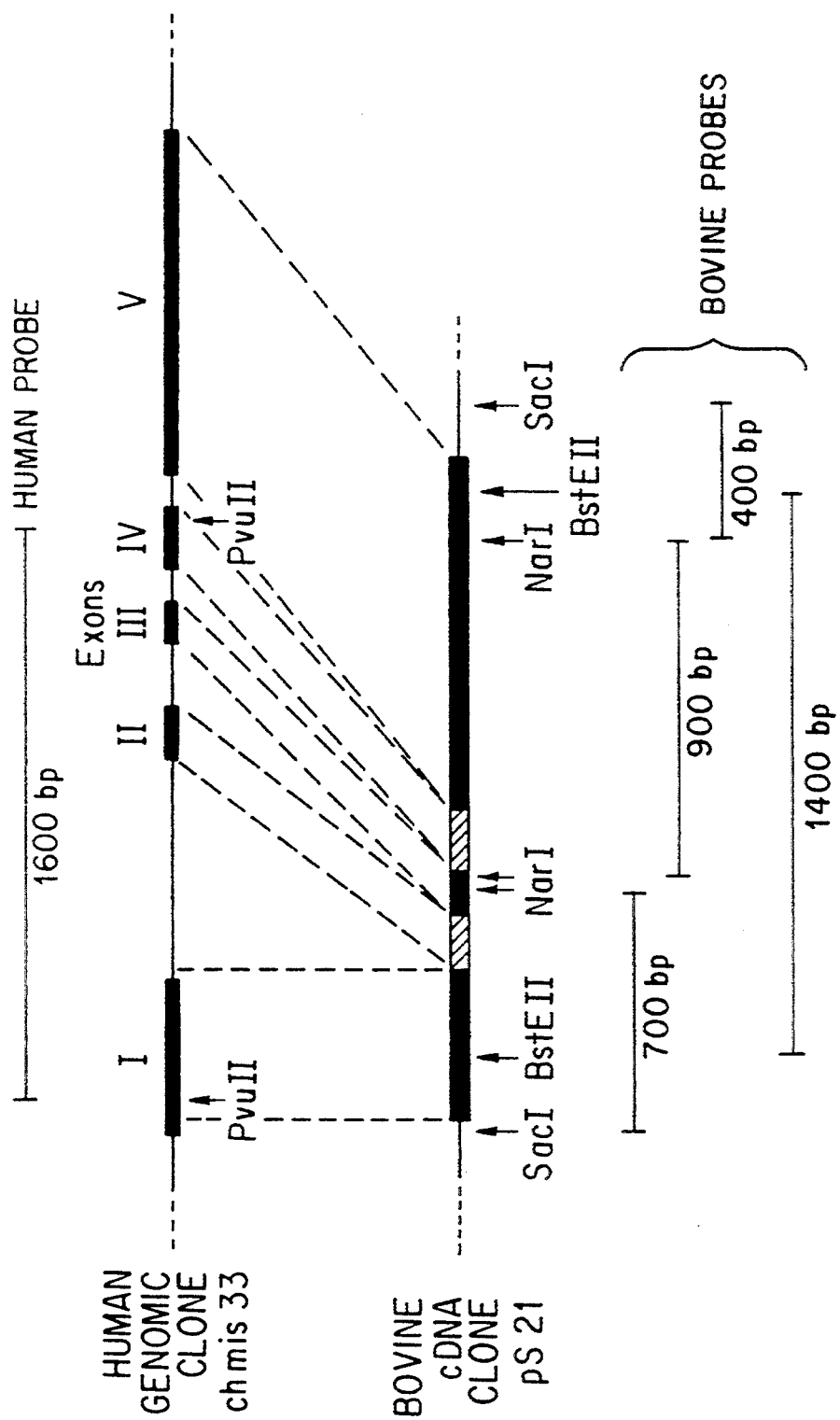
FIG. 5 depicts the human genomic clone chmis33 and compares it with the bovine cDNA clone pS21. The solid blocks are exons which contain the protein coding regions.

Using the bovine cDNA clone pS21, we isolated the human clone (chmis33) from a human cosmid library. We sequenced the entire gene, which is contained in five exons that span a distance of 2.8 kb. FIG. 5 shows the general structure of the human gene, while FIG. 6A–6K show the nucleotide sequence. In FIG. 6A–6K the first 100 bp contain the human promoter and the 5' untranslated region. This is followed by 2622 bp that contain the five protein coding regions, which are indicated below the DNA sequence. The last 112 bp are the 3' untranslated region.

EXAMPLE 5

CONSTRUCTION OF A FULL LENGTH HUMAN cDNA

Figure 8:
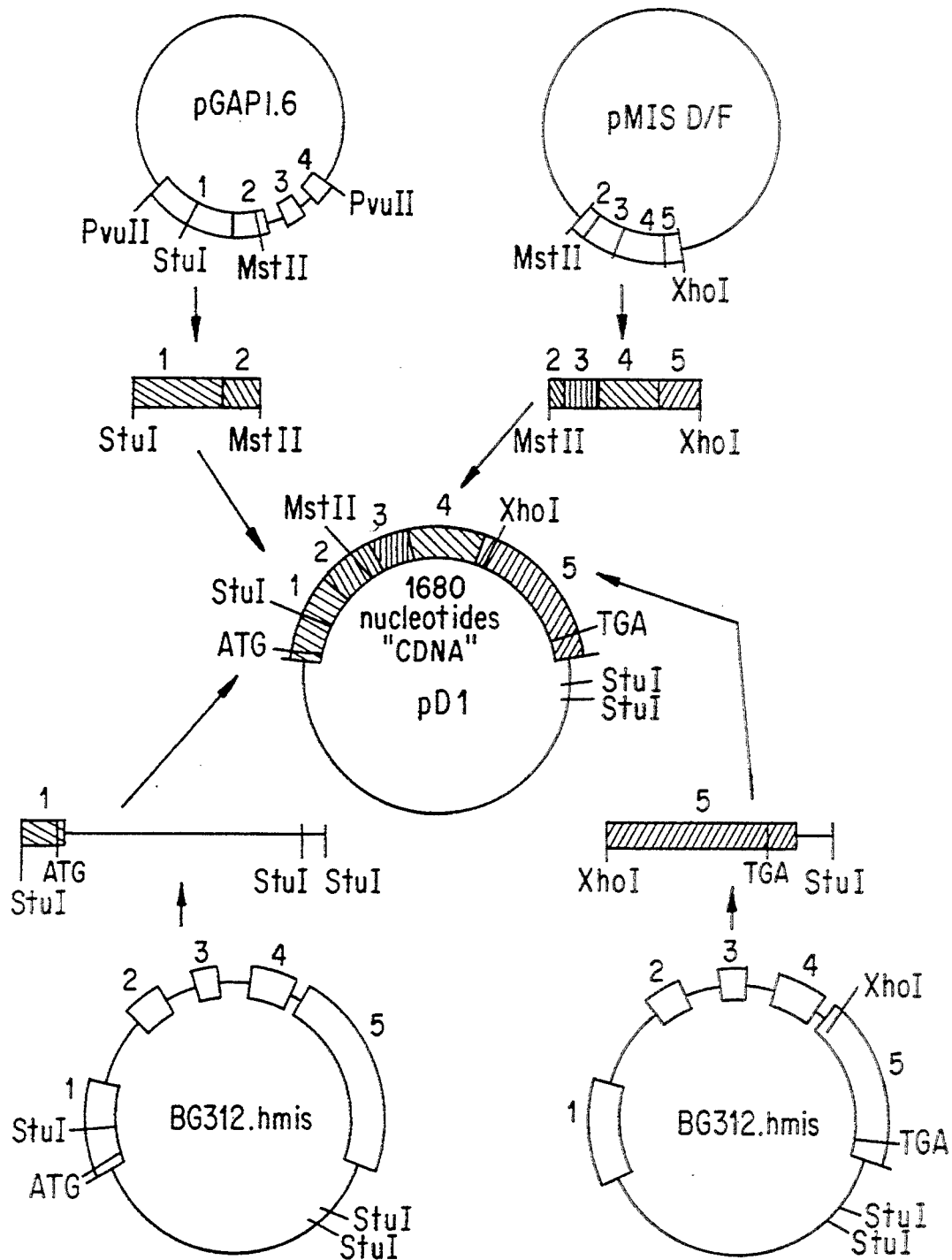
FIG. 8 depicts the construction of plasmid pD1 which contains the full length cDNA and may be used to express the human DNA sequence of the invention.

We constructed a full length human cDNA in pBG312 (pD1) via a four way ligation shown in FIG. 8 with the following four fragments: 1) 271 bp StuI-MstII fragment from pGAP1.6; 2) 323 bp MstII-XhoI fragment from pMIS D/F; 3) 1299 bp XhoI-StuI fragment from pBG312.hmis; and 4) the 6251 bp StuI fragment from pBG312.hmis. The construction of pBG312.hmis is described in Example 7. The construction of pGAP1.6 and pMIS D/F are described below.

We generated plasmid pGAP1.6 which is missing the first intron through gapped mutagenesis. The 1600 bp PvuII fragment from chmis 33 (FIG. 5) was subcloned into the SmaI site of pUC18 to generate pUC18.PV2. This plasmid was linearized with SspI, denatured and then annealed to denatured pUC18.PV2 digested with StuI and MstII. This permitted the formation of hybrid duplexes between the SspI digested and the StuI and MstII digested pUC18.PV2. We then annealed an oligomer containing sequence from the 3' end of exon 1 and the 5' end of exon 2 (i.e., missing the first intron) to the hybrid duplexes. We used DNA polymerase I-large fragment to synthesize the second strand. We then transformed E. coli and screened colonies with the $^{32}$P-labeled oligomer. We identified a positive clone, pGAP1.6, and sequenced it to verify that the first intron was deleted. We isolated the 271 bp StuI-MstII fragment for the four way ligation (FIG. 8).

The construction of pMIS D/F in which introns 2, 3, and 4 are deleted involved two steps. In the first step, we isolated a lambda clone λMIS21 from a λgt10 cDNA library made from RNA that was isolated from COS cells transfected with pBG312.hmis (see Example 7). We sequenced the insert of this clone and determined that introns 3 and 4 were missing. In the second step, we isolated the 269 bp AvaI-XhoI fragment of MIS21 that spans from exon 3 to the 5' end of exon 5 and ligated it to a linker and the XhoI-HindIII fragment of vector pcHSA35 (described below). The linker was made by synthesizing two oligomers of 63 nucleotides containing the DNA sequence from the MstII site in exon 2 to the AvaI site in exon 3, but missing intron 2. In addition, the linker contained DNA sequence encoding a HindIII site at the 5' end (adjacent to the MstII site). The three way ligation produced plasmid pMIS D/F which is missing introns 2, 3, and 4. The 323 bp MstII-XhoI fragment was then isolated for the four way ligation (FIG. 8).

pcHSA35 is a plasmid constructed from plasmid pcHSA36. pcHSA36 was deposited in the culture collection of the American Type Culture Collection in Rockville, Md. on Dec. 9, 1982 and identified there as HSA-B and assigned ATCC accession number 39253. pcHSA36 was digested with restriction enzyme BstEII to completion, blunt ended with the exonuclease Ba131, followed by digestion with the restriction enzyme BamHI and the sticky ends blunt ended with DNA polymerase I-large fragment. The resulting linear plasmid was circularized by ligation and a plasmid containing a single XhoI site was isolated and designated pcHSA35.

EXAMPLE 6
EXPRESSION OF THE BOVINE GENE

We combined sequences from the bovine cDNA clone (pX21) with sequences from the bovine genomic cosmid clone (cbmis.15) in the animal cell expression vector pBG311 in order to express the entire bovine protein in COS cells and CHO cells (FIG. 4). Expression may be detected by analyzing RNA by Northern and S1 analysis. Also, recombinant bovine MIS may be detected by a RIA and by the organ culture assay. *E. coli* strain JM83 harboring plasmid pBG311.bmis has been deposited with the In Vitro International Inc. depository as Deposit No. IVI 10090.

EXAMPLE 7
EXPRESSION OF THE HUMAN GENE IN ANIMAL CELLS

To express the human MIS gene in animal cells, we inserted the 4.5 kb AflII fragment from chmis33 into the animal cell expression vectors pBG311 and pBG312 described by Cate et al. (*Cell*, 45, 685–698 (1986)), to produce pBG311.hmis and pBG312.hmis, respectively (FIG. 7). pBG311 uses the SV40 early promoter, while pBG312 uses the adenovirus-2 major late promoter to drive expression. We introduced these constructions into COS cells (defective SV40 transformed Simian cells; Gluzman, *Cell.*, 23, 175–182 (1981)) for transient expression and later into Chinese hamster ovary (CHO) cells (Chasin and Urlaub, *Proc. Natl. Acad. Sci. USA*, 77, 4216–4220 (1980)) for stable expression.

We transfected COS cells with pBG312.hmis using the DEAE/dextran method of Sompayrac and Danna (*Proc. Natl. Acad. Sci. USA*, 78, 7575–7578 (1981)). We used an S1 analysis to demonstrate that the human MIS gene is transcribed and that the RNA is spliced. We then used an organ culture assay (Donahoe et al., *J. Surg. Res.*, 23, 141–148 (1977)) to demonstrate that COS cells transfected with the human MIS gene secrete biologically active MIS. Conditioned media from COS cells transfected with pBG312.hmis produced grade 3 regression of the Mullerian duct in this assay, while control media and conditioned media from COS cells transfected with the human tissue plasminogen activator cDNA did not cause regression. This demonstrated that COS cells transfected with the human MIS gene secrete biologically active MIS that causes regression of the rat Mullerian duct in vitro.

To express the human MIS gene in CHO cells, we introduced plasmid pBG311.hmis and plasmid pSV2DHFR (Subramani et al., *Mol. Cell Biol.*, 1, 854–864 (1981)) into CHO cells deficient in dihydrofolate reductase using the procedure of Scahill et al., *Proc. Natl. Acad. Sci. USA*, 80, 4654–4658 (1983). We selected twenty-five clones that grew in medium lacking nucleosides and expanded them to T75 flasks. We isolated total RNA from these clones and analyzed for the presence of human MIS mRNA by an S1 assay; ten of the clones contained human MIS mRNA. We then tested the conditioned medium from one cell line positive for MIS mRNA, 311-22, in the organ culture assay; it produced grade 3–4 regression of the Mullerian duct in the organ culture assay, while conditioned medium from a control cell line G2 did not cause regression.

We partially purified the human recombinant MIS from the conditioned medium of cell line 311-22 using lentil-lectin chromatography and analyzed on Western blots with two different antibodies (Towbin et al., *Proc. Natl. Acad. Sci. USA*, 76, 4350 (1979)). One antibody was raised against denatured bovine MIS while the other was raised against a peptide of human MIS. In both cases, the antibodies recognized a protein in the conditioned medium of 311-22 with a molecular weight of approximately 70,000. There was no detectable protein in the conditioned medium of control CHO cell line G2. This demonstrated that human MIS made in CHO cells is glycosylated to the same or approximately the same level as bovine MIS isolated from newborn testis. We have also labeled MIS produced in CHO cells by growing the cells for 24 hours in the presence of [$^3$H]-glucosamine. The glycoproteins were then batch purified from the conditioned medium with lentil-lectin-Sepharose, and MIS was immunoprecipitated with the antibody against denatured bovine MIS.

We have confirmed the identity and structure of recombinant MIS. We concentrated conditioned serum free medium from clone 311-2A9B7 (amplified in 30 nM methotrexate) by ultrafiltration and extracted the glycoproteins with lentil-lectin. A 70 Kd band was detected by Coomassie staining after SDS-PAGE, that was not present in the conditioned medium of a cell line that served as a negative control. We performed 2-D gel electrophoresis (nonreducing-reducing) which demonstrated that the human recombinant MIS is a disulfide reducible dimer. CNBr mapping of the protein generated a pattern of fragments that was consistent with the known methionine distribution of MIS, We partially purified 20 μg of the 70 kd band from 400 ml of conditioned serum-free medium by a combination of lentil-lectin and gel filtration chromatography. We electroeluted the protein from a preparative SDS gel and performed protein microsequence analysis. The amino terminus of the recombinant protein is L R A E E, which demonstrates that human MIS is correctly processed by the CHO cells.

The level of expression of MIS in the CHO cell lines can be increased by methotrexate-driven gene amplification as described by Kaufman and Sharp (*J. Mol. Biol.*, 159, 601–621 (1982)).

*E. coli* strain JA221 harboring plasmid pBG312.hmis has been deposited with In Vitro International Inc. depository as Deposit No. IVI 10089.

EXAMPLE 8

EXPRESSION OF THE HUMAN cDNA

The plasmid pD1, described in Example 5 contains the full length cDNA sequence in the animal expression vector pBG312. Plasmid pD1 can be introduced into COS cells using the DEAE/dextran protocol of Sompayrac and Danna (*Proc. Natl. Acad. Sci. USA* 78, 7575–7578 (1981)) in order to produce human MIS. The entire human cDNA sequence can be removed from plasmid pD1 using AflII and inserted into the SmaI site of pBG311 in order to express the human cDNA in CHO cells.

The insert of pD1 containing the full length human cDNA insert can be removed and inserted into *E. coli* and yeast vectors allowing expression of human MIS in *E. coli* and yeast. These constructions may contain DNA sequences encoding for the complete human MIS protein or DNA sequences encoding for the mature human MIS protein.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A composition comprising human Mullerian Inhibiting (MIS) Substance of heterologous host cell proteins wherein said human MIS has an amino acid sequence selected from the group consisting of:

MRDLPSTSLALVLSALGALLGTEAL
RAEEPAVGTSGLIFREDLWPPGIP
QEPLCLVALGGDSNGSSSPLRVVGA
LSAYEQAFLGAVQRATWGPRDLATF
GVCNTGDRQAALPSLRRLGAWLRDP
GGQRLVVLHLEEVTWEPTPSLRFQE
PPPGGAGPPELALLVLYPGPGPEVT
VTRAGLPGAQSLCPSRDTRYLVAV
DRPAGAWRGSGLALTLQPRGEDSRL
STARLQALLFGDDHRCFTRMTPALL
LLPRSEPAPLPAHGQLDTVPFPPPR
PSAELEESPPSADPFLETLTRLVRA
LRVPPARASAPRLALDPDALAGFPQ
GLVNLSDPAALERLLDGEEPLLLLL
RPTAATTGDPAPLHDPTSAPWATAL
ARRVAAELQAAAAELRSLPGLPPAT
APLLARLLALCPGGPGGLGDPLRAL
LLLKALQGLRVEWRGRDPRGPGRAQ
RSAGATAADGPCALRELSVDLRAER
SVLIPETYQANNCQGVCGWPQSDRN
PRYGNHVVLLLKMQARGAALARPPC
CVPTAYAGKLLISLSEERISAHHVP
NMVATECGCR;

and

LRAEEPAVGTSGLIFREDLDWPPGI
PQEPLCLVALGGDSNGSSSPLRVVG
PQEPLCLVALGGDSNGSSSPLRVVG
ALSAYEQAFLGAVQRARWGPRDLAT
FGVCNTGDRQAALPSLRRLGAWLRD
PGGQRLVVLHLEEVTWEPTPSLRFQ
EPPPGGAGPPELALLVLYPGPGPEV
TVTRAGLPGAQSLCPSRDTRYLVLA
VDRPAGAWRGSGLALTLQPRGEDSR
LSTARLQALLFGDDHRCFTRMTPAL
LLLPRSEPAPLPAHGQLDTVPFPPP
RPSAELEESPPSADPFLETLTRLVR
ALRVPPARASAPRLALDPDALAGFP
QGLVNLSDPAALERLLDGEEPLLLL
LRPTAATTGDPAPLHDPTSAPWATA
LARRVAAELQAAAAELRSLPGLPPA
TAPLLARLLALCPGGPGGLGDPLRA
LLLLKALQGLRVEWRGRDPRGPGRA
QRSAGATAADGPCALRELSVDLRAE
RSVLIPETYQANNCQGVCGWPQSDR
NPRYGNHVVLLLKMQARGAALARPP
CCVPTAYAGKLLISLSEERISAHHV
PNMVATECGCR.

* * * * *

UNITED STATES PATENT AND TRADEMARK OFFICE
CERTIFICATE OF CORRECTION

PATENT NO. : 5,427, 780
DATED : June 27, 1995
INVENTOR(S) : Cate, et al

It is certified that error appears in the above-indentified patent and that said Letters Patent is hereby corrected as shown below:

Column 8, beginning on line 43, the amino acid sequence should appear as follows:

MRDLPLTSLALVLSALGALLGTEALRAEEPAVGTSGLIFREDLDWPPGIP

QEPLCLVALGGDSNGSSSPLRVVGALSAYEQAFLGAVQRARWGPRDLATF

GVCNTGDRQAALPSLRRLGAWLRDPGGQRLVVLHLEEVTWEPTPSLRFQE

PPPGGAGPPELALLVLYPGPGPEVTVTRAGLPGAQSLCPSRDTRYLVLAV

DRPAGAWRGSGLALTLQPRGEDSRLSTARLQALLFGDDHRCFTRMTPALL

LLPRSEPAPLPAHGQLDTVPFPPPRPSAELEESPPSADPFLETLTRLVRA

LRVPPARASAPRLALDPDALAGFPQGLVNLSDPAALERLLDGEEPLLLLL

RPTAATTGDPAPLHDPTSAPWATALARRVAAELQAAAAELRSLPGLPPAT

APLLARLLALCPGGPGGLGDPLRALLLLKALQGLRVEWRGRDPRGPGRAQ

RSAGATAADGPCALRELSVDLRAERSVLIPETYQANNCQGVCGWPQSDRN

PRYGNHVVLLLKMQARGAALARPPCCVPTAYAGKLLISLSEERISAHHVP

NMVATECGCR

UNITED STATES PATENT AND TRADEMARK OFFICE
CERTIFICATE OF CORRECTION

PATENT NO. : 5,427,780
DATED : June 27, 1995
INVENTOR(S) : Cate, et al

Page 2 of 5

It is certified that error appears in the above-indentified patent and that said Letters Patent is hereby corrected as shown below:

Column 8, beginning on line 59, the amino acid sequence should appear as follows:

LRAEEPAVGTSGLIFREDLDWPPGIPQEPLCLVALGGDSNGSSSPLRVVG

ALSAYEQAFLGAVQRARWGPRDLATFGVCNTGDRQAALPSLRRLGAWLRD

PGGQRLVVLHLEEVTWEPTPSLRFQEPPPGGAGPPELALLVLYPGPGPEV

TVTRAGLPGAQSLCPSRDTRYLVLAVDRPAGAWRGSGLALTLQPRGEDSR

LSTARLQALLFGDDHRCFTRMTPALLLLPRSEPAPLPAHGQLDTVPFPPP

RPSAELEESPPSADPFLETLTRLVRALRVPPARASAPRLALDPDALAGFP

QGLVNLSDPAALERLLDGEEPLLLLLRPTAATTGDPAPLHDPTSAPWATA

LARRVAAELQAAAAELRSLPGLPPATAPLLARLLALCPGGPGGLGDPLRA

LLLLKALQGLRVEWRGRDPRGPGRAQRSAGATAADGPCALRELSVDLRAE

RSVLIPETYQANNCQGVCGWPQSDRNPRYGNHVVLLLKMQARGAALARPP

CCVPTAYAGKLLISLSEERISAHHVPNMVATECGCR

UNITED STATES PATENT AND TRADEMARK OFFICE
CERTIFICATE OF CORRECTION

PATENT NO. : 5,427,780  
DATED : June 27, 1995  
INVENTOR(S) : Cate, et al

It is certified that error appears in the above-indentified patent and that said Letters Patent is hereby corrected as shown below:

Column 25, line 38 (claim 1), "Substance of heterologous" is incorrect and should be replaced with —Substance in the presence of heterologous—; and beginning on line 42, the amino acid sequence should appear as follows:

MRDLPLTSLALVLSALGALLGTEALRAEEPAVGTSGLIFREDLDWPPGIP

QEPLCLVALGGDSNGSSSPLRVVGALSAYEQAFLGAVQRARWGPRDLATF

GVCNTGDRQAALPSLRRLGAWLRDPGGQRLVVLHLEEVTWEPTPSLRFQE

PPPGGAGPPELALLVLYPGPGPEVTVTRAGLPGAQSLCPSRDTRYLVLAV

DRPAGAWRGSGLALTLQPRGEDSRLSTARLQALLFGDDHRCFTRMTPALL

LLPRSEPAPLPAHGQLDTVPFPPPRPSAELEESPPSADPFLETLTRLVRA

LRVPPARASAPRLALDPDALAGFPQGLVNLSDPAALERLLDGEEPLLLLL

RPTAATTGDPAPLHDPTSAPWATALARRVAAELQAAAAELRSLPGLPPAT

APLLARLLALCPGGPGGLGDPLRALLLLKALQGLRVEWRGRDPRGPGRAQ

RSAGATAADGPCALRELSVDLRAERSVLIPETYQANNCQGVCGWPQSDRN

PRYGNHVVLLLKMQARGAALARPPCCVPTAYAGKLLISLSEERISAHHVP

NMVATECGCR

UNITED STATES PATENT AND TRADEMARK OFFICE
CERTIFICATE OF CORRECTION

PATENT NO. : 5,427,780

DATED : June 27, 1995

INVENTOR(S) : Cate, et al

It is certified that error appears in the above-indentified patent and that said Letters Patent is hereby corrected as shown below:

Column 26, beginning on line 23 (in claim 1), the amino acid sequence should appear as follows:

LRAEEPAVGTSGLIFREDLDWPPGIPQEPLCLVALGGDSNGSSSPLRVVG

ALSAYEQAFLGAVQRARWGPRDLATFGVCNTGDRQAALPSLRRLGAWLRD

PGGQRLVVLHLEEVTWEPTPSLRFQEPPPGGAGPPELALLVLYPGPGPEV

TVTRAGLPGAQSLCPSRDTRYLVLAVDRPAGAWRGSGLALTLQPRGEDSR

LSTARLQALLFGDDHRCFTRMTPALLLLPRSEPAPLPAHGQLDTVPFPPP

RPSAELEESPPSADPFLETLTRLVRALRVPPARASAPRLALDPDALAGFP

QGLVNLSDPAALERLLDGEEPLLLLLRPTAATTGDPAPLHDPTSAPWATA

LARRVAAELQAAAAELRSLPGLPPATAPLLARLLALCPGGPGGLGDPLRA

UNITED STATES PATENT AND TRADEMARK OFFICE
CERTIFICATE OF CORRECTION

PATENT NO. : 5,427,780
DATED : June 27, 1995
INVENTOR(S) : Cate, et al

It is certified that error appears in the above-indentified patent and that said Letters Patent is hereby corrected as shown below:

LLLLKALQGLRVEWRGRDPRGPGRAQRSAGATAADGPCALRELSVDLRAE

RSVLIPETYQANNCQGVCGWPQSDRNPRYGNHVVLLLKMQARGAALARPP

CCVPTAYAGKLLISLSEERISAHHVPNMVATECGCR

Signed and Sealed this

Sixteenth Day of January, 1996

Attest:

BRUCE LEHMAN

*Attesting Officer*  *Commissioner of Patents and Trademarks*